(12) United States Patent
Zhao et al.

(10) Patent No.: US 7,897,647 B2
(45) Date of Patent: *Mar. 1, 2011

(54) RELEASABLE POLYMERIC CONJUGATES BASED ON ALIPHATIC BIODEGRADABLE LINKERS

(75) Inventors: Hong Zhao, Edison, NJ (US); Richard B. Greenwald, Somerset, NJ (US); Annapurna Pendri, South Glastonbury, CT (US)

(73) Assignee: Enzon Pharmaceuticals, Inc., Bridgewater, NJ (US)

( * ) Notice: Subject to any disclaimer, the term of this patent is extended or adjusted under 35 U.S.C. 154(b) by 671 days.

This patent is subject to a terminal disclaimer.

(21) Appl. No.: 11/502,108

(22) Filed: Aug. 9, 2006

(65) Prior Publication Data
US 2006/0286065 A1    Dec. 21, 2006

Related U.S. Application Data

(63) Continuation of application No. 10/218,167, filed on Aug. 13, 2002, now Pat. No. 7,122,189.

(51) Int. Cl.
*A01N 33/08* (2006.01)
(52) U.S. Cl. .............. 514/668; 514/715; 514/718; 424/94.1; 424/179.1; 424/181.1; 424/193.1; 424/194.1
(58) Field of Classification Search .......... 514/668, 514/715, 716; 424/179.1, 181.1, 193.1, 194.1
See application file for complete search history.

(56) References Cited

U.S. PATENT DOCUMENTS

| | | |
|---|---|---|
| 3,888,797 A | 6/1975 | Marumo |
| 4,179,337 A | 12/1979 | Davis et al. |
| 5,643,575 A | 7/1997 | Martinez et al. |
| 5,679,711 A | 10/1997 | Carrell et al. |
| 5,919,455 A | 7/1999 | Greenwald et al. |
| 6,113,906 A | 9/2000 | Greenwald et al. |
| 7,087,229 B2 | 8/2006 | Zhao et al. |
| 7,122,189 B2 | 10/2006 | Zhao et al. |
| 7,273,845 B2 | 9/2007 | Zhao et al. |
| 2005/0197290 A1 | 9/2005 | Zhao et al. |

FOREIGN PATENT DOCUMENTS

| | | |
|---|---|---|
| DE | 4135115 A | 4/1993 |
| EP | 1186613 | 3/2002 |
| JP | 06240091 | 8/1994 |
| WO | 03/070726 | 8/2003 |
| WO | 2004/014424 | 2/2004 |
| WO | 2004/044222 | 5/2004 |
| WO | 2004/085386 | 10/2004 |
| WO | 2004/092191 | 10/2004 |
| WO | 2004/108070 | 12/2004 |

OTHER PUBLICATIONS

Zhao, H., et al., Linear and Branched Bicin Linkers for Releasable PEGylation . . . , Bioconjugate Chemistry, vol. 17: 341-351, 2006.
Suggs, W. J., et al., Facile Hydrolysis and Formation of Amine Bonds . . . , Tetrahedron Letters, vol. 38: 2227-2230, 1997.
Pasut, G., et al., Protein, Peptide and Non-peptide Drug PEGylation for . . . , Expert Opinion Therapeutic Patents, 14: 859-894, 2004.
Greenwald, R. B., et al., A New Aliphatic Amino Prodrug System for . . . , J. Med. Chem., 47: 726-734, 2004.
Caplus Database, accession No. 1995:235122, abstract and structures for JP 06240091, printed on Feb. 3, 2006 from STN.
Derwent Database, accession No. 1994-313850, abstract for JP 06240091, printed on Feb. 3, 2006 from WEST.

*Primary Examiner*—Michael G Wityshyn
*Assistant Examiner*—Susan Hanley
(74) *Attorney, Agent, or Firm*—Lucas & Mercanti, LLP

(57) ABSTRACT

Activated polymeric bicine derivatives such as

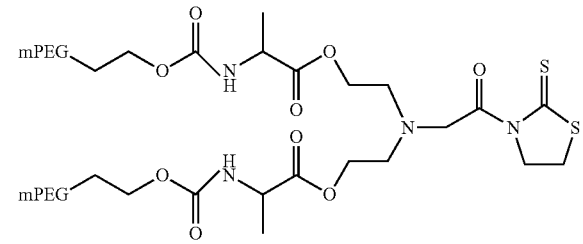

as well as conjugates made therewith are disclosed. Methods of making and using the bicine derivatives are also disclosed.

44 Claims, 17 Drawing Sheets

RELEASABLE POLYMERIC CONJUGATES BASED ON ALIPHATIC BIODEGRADABLE LINKERS

CROSS-REFERENCE TO RELATED APPLICATIONS

This patent application is a continuation of U.S. Ser. No. 10/218,167 filed Aug. 13, 2002, now U.S. Pat. No. 7,122,189, the contents of which are incorporated by reference herein in its entirety.

FIELD OF THE INVENTION

The present invention relates to branched polymers which are useful in extending the in vivo circulating life of biologically active materials. The invention also relates to conjugates made with the polymers.

BACKGROUND OF THE INVENTION

Some of the initial concepts of coupling peptides or polypeptides to poly(ethylene glycol) PEG and similar water-soluble poly(alkylene oxides) are disclosed in U.S. Pat. No. 4,179,337, the disclosure of which is incorporated herein by reference. Polypeptides modified with these polymers exhibit reduced immunogenicity/antigenicity and circulate in the bloodstream longer than unmodified versions.

To conjugate poly(alkylene oxides), one of the hydroxyl end-groups is converted into a reactive functional group. This process is frequently referred to as "activation" and the product is called an "activated poly(alkylene oxide)". Other substantially non-antigenic polymers are similarly "activated" or functionalized.

The activated polymers are reacted with a therapeutic agent having nucleophilic functional groups that serve as attachment sites. One nucleophilic functional group commonly used as an attachment site is the ε-amino groups of lysines. Free carboxylic acid groups, suitably activated carbonyl groups, oxidized carbohydrate moieties and mercapto groups have also been used as attachment sites.

Insulin and hemoglobin were among the first therapeutic agents conjugated. These relatively large polypeptides contain several free ε-amino attachment sites. A sufficient number of polymers could be attached to reduce immunogenicity and increase the circulating life without significant loss of biologic activity.

Excessive polymer conjugation and/or conjugation involving a therapeutic moiety's active site where groups associated with bioactivity are found, however, often result in loss of activity and thus therapeutic usefulness. This is often the case with lower molecular weight peptides which have few attachment sites not associated with bioactivity. Many non-peptide therapeutics also lack a sufficient number of attachment sites to obtain the benefit of polymeric modification.

One suggestion for overcoming the problems discussed above is to use longer, higher molecular weight polymers. These materials, however, are difficult to prepare and expensive to use. Further, they provide little improvement over more readily available polymers.

Another alternative suggested is to attach two strands of polymer via a triazine ring to amino groups of a protein. See, for example, Enzyme, 26, 49-53 (1981) and Proc. Soc. Exper. Biol. Med., 188, 364-9 (1988). Triazine, however, is a toxic substance which is difficult to reduce to acceptable levels after conjugation. In addition, triazine is a planar group and can only be double-polymer substituted. The planar structure rigidly locks the two polymer chains in place. This limits the benefits of polymer conjugation to about the same as that obtained by increasing polymer chain length. Thus, non-triazine-based activated polymers would offer substantial benefits to the art.

In the above-mentioned cases, however, the biologically active polymer conjugates were formed having substantially hydrolysis-resistant bonds (linkages) between the polymer and the parent biologically-active moiety. Thus, long-lasting conjugates which are permanently linked rather than prodrugs per se (where the parent molecule is eventually liberated in vivo) were prepared.

Commonly assigned U.S. Pat. Nos. 5,643,575, 5,919,455 and 6,113,906 disclose additional improvements relating to multiple-strands of PEG sharing a common point of attachment to a nucleophile via an aliphatic linker. Unlike the earlier triazine-based branched polymer conjugates, the aliphatic linkers allow the artisan to avoid the toxicities of triazine as well as provide other useful advantages.

In addition, over the years, several methods of preparing prodrugs have also been suggested. Prodrugs include chemical derivatives of a biologically-active parent compound which, upon administration, will eventually liberate the active parent compound in vivo. Use of prodrugs allows the artisan to modify the onset and/or duration of action of a biologically-active compound in vivo. Prodrugs are often biologically inert or substantially inactive forms of the parent or active compound. The rate of release of the active drug is influenced by several factors including the rate of hydrolysis of the linker which joins the parent biologically active compound to the prodrug carrier.

Some prodrugs based on ester or phosphate linkages have been reported. In most cases, the particular type of ester linkage used to form the prodrug provides $t_{1/2}$ for hydrolysis of up to several days in aqueous environments. Although one would expect a prodrug to have been formed, most of the conjugate is eliminated prior to sufficient hydrolysis being achieved in vivo. It would therefore be preferable to provide prodrugs which have a linkage which allows more rapid hydrolysis of the polymer-drug linkage in vivo so as to generate the parent drug compound more rapidly.

Prodrugs based on amide or carbamate linkages have also been reported. In general, amide bonds are known to be highly resistant to hydrolysis. However, it has recently been found that the C-terminal amides of ε-amino acids are readily hydrolyzed at 25° C. and pH 7 when the N-terminus is N-hydroxyethylated with one or two hydroxyethyl groups. Bis N-2-hydroxyethyl glycine (bicine) is a key molecule in such hydrolysis reactions. Such bicine groups have not, however, been employed in the synthesis of prodrugs, especially polymer-based prodrugs.

There still exists a need to improve polymer-based prodrugs. The present invention addresses such needs.

SUMMARY OF THE INVENTION

In one aspect of the invention, compounds of Formula (I) are provided: (I)

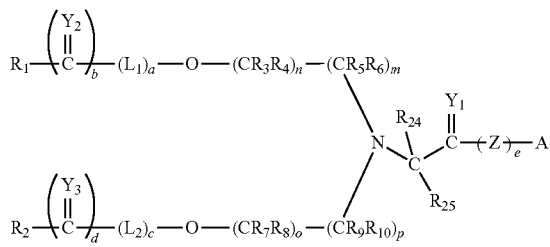

wherein:

$R_1$ and $R_2$ are independently selected from the group consisting of substantially non-antigenic polymer residues, $C_{1-6}$ alkyls, aralkyls, and terminal branching groups;

Z is selected from among moieties actively transported into a target cell, hydrophobic moieties, bifunctional linking moieties and combinations thereof;

$Y_{1-3}$ are independently selected from among O, S or $NR_{11}$;

$L_1$ and $L_2$ are independently selected bifunctional linkers;

$R_3$-$R_{11}$, $R_{24}$ and $R_{25}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

A is selected from among leaving groups, functional groups and residues of amine-containing agents and OH;

a and c are each independently 0 or a positive integer;

b, d and e are independently 0 or 1; and m, n, o, and p are independently selected positive integers.

Another aspect of the invention includes bifunctional compounds that are formed when at least one of ($R_1$) and ($R_2$) is a polymeric residue which includes both an alpha and omega terminal linking group. In this aspect of the invention, the artisan is capable of attaching two equivalents of a biologically active agent drug, protein, polypeptide, etc. to the polymeric (preferably PEG) bicine system. An example of such a bifunctional polymer conjugate is illustrated below as formula (IIa) and (IIb):

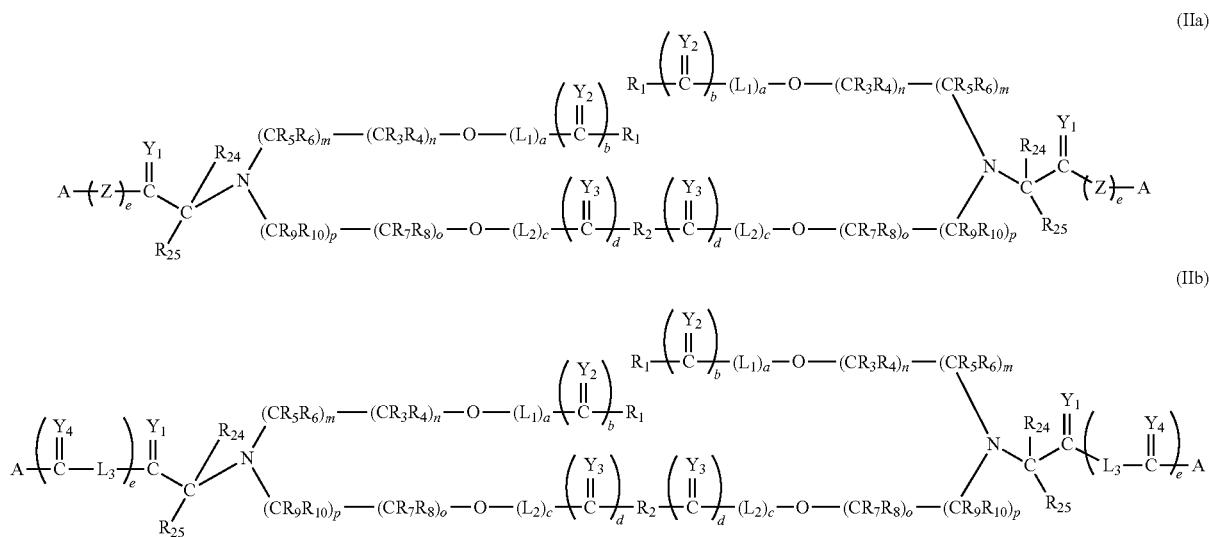

wherein all variables are as described above and $Y_4$ is O, S or $NR_{11}$ and $L_3$ is a bifunctional linker.

Methods of preparing the compounds of the present invention and methods of treatment using the same are also provided.

For purposes of the present invention, the term "residue" shall be understood to mean that portion of a compound, to which it refers, that remains after it has undergone a substitution reaction in which the polymeric prodrug carrier portion has been attached.

For purposes of the present invention, the term "polymeric residue" or "PEG residue" shall each be understood to mean that portion of the polymer or PEG which remains after it has undergone a reaction with a biologically active compound.

For purposes of the present invention, the term "alkyl" shall be understood to include straight, branched, substituted, e.g. halo-, alkoxy-, nitro-, $C_{1-12}$ alkyls, $C_{3-8}$ cycloalkyls or substituted cycloalkyls, etc.

For purposes of the present invention, the term "substituted" shall be understood to include adding or replacing one or more atoms contained within a functional group or compound with one or more different atoms.

For purposes of the present invention, substituted alkyls include carboxyalkyls, aminoalkyls, dialkylaminos, hydroxyalkyls and mercaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkynylaminos, hydroxyalkynyls and mercaptoalkynyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxy-thiophene; alkoxy includes moieties such as methoxy; and phenoxy includes moieties such as 3-nitro-phenoxy. Halo—shall be understood to include fluoro, chloro, iodo and bromo.

The term "sufficient amounts" for purposes of the present invention shall mean an amount which achieves a therapeutic effect as such effect is understood by those of ordinary skill in the art.

For purposes of the present invention, "effectively non-antigenic" and "substantially non-antigenic" shall be understood to include all polymeric materials understood in the art as being substantially non-toxic and not eliciting an appreciable immune response in mammals.

For purposes of the present invention, a "positive integer" shall be understood to mean a positive whole number, preferably from about 1 to 6 and more preferably 1 or 2.

One chief advantage of the present invention is that the bicine linker allows for the manipulation of the hydrolysis rate of the prodrug, thereby releasing the native entities at various rates in vivo as well as in vitro. For example, various bifunctional moieties, including amino acid or short peptide residues can be included as part of any of $L_{1-3}$ to modulate the rate of hydrolysis of the prodrug and/or cellular uptake, etc. in vivo and in vitro.

Another advantage of the invention is that the target compounds delivered via the polymeric transport system often demonstrate a measurable increase in aqueous solubility and circulating life in vivo.

DETAILED DESCRIPTION OF THE INVENTION

A. Formula (I)

Figure 1:
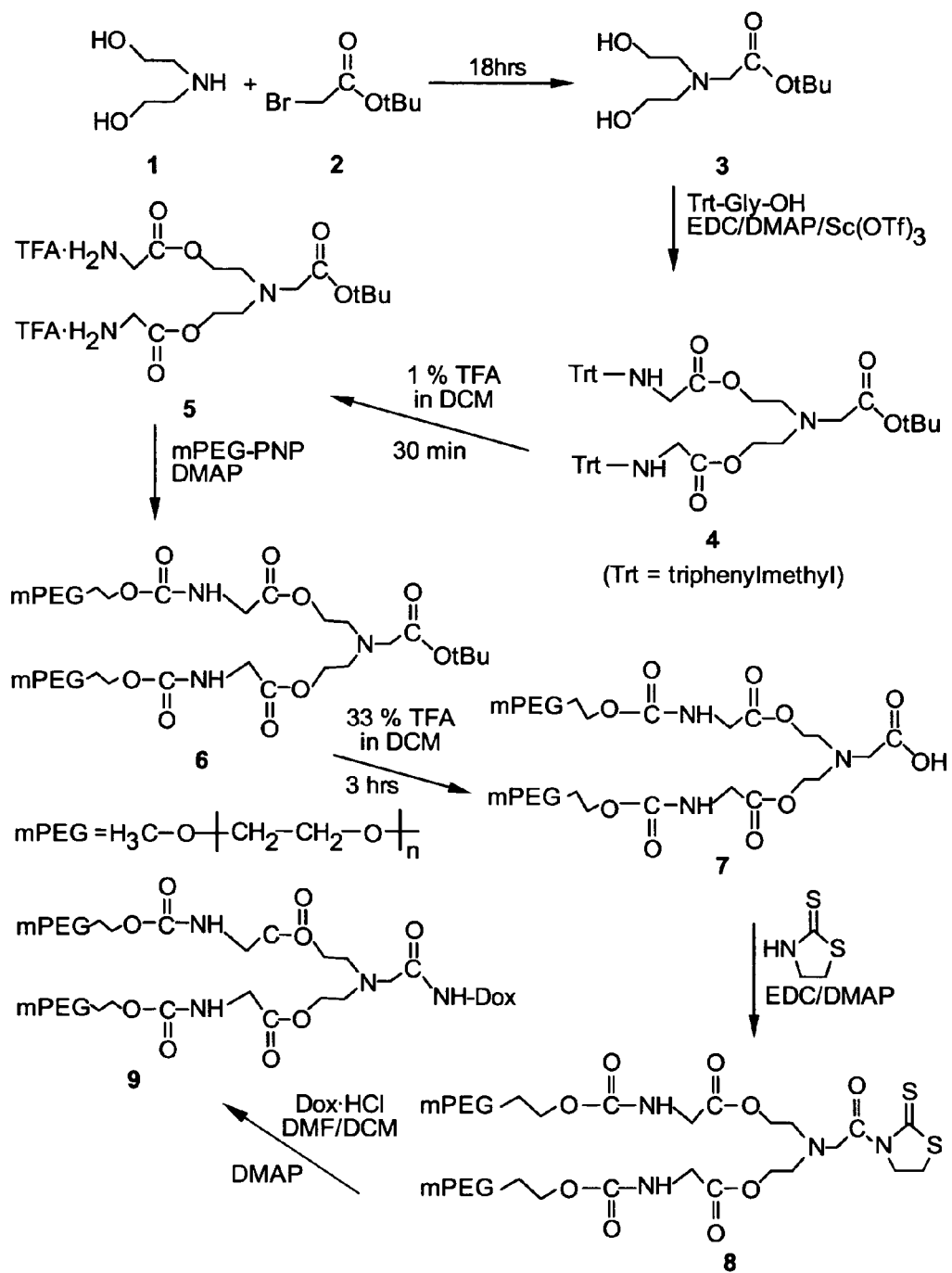
FIG. 1 provides reaction schemes corresponding to examples 1-7.
Figure 2:
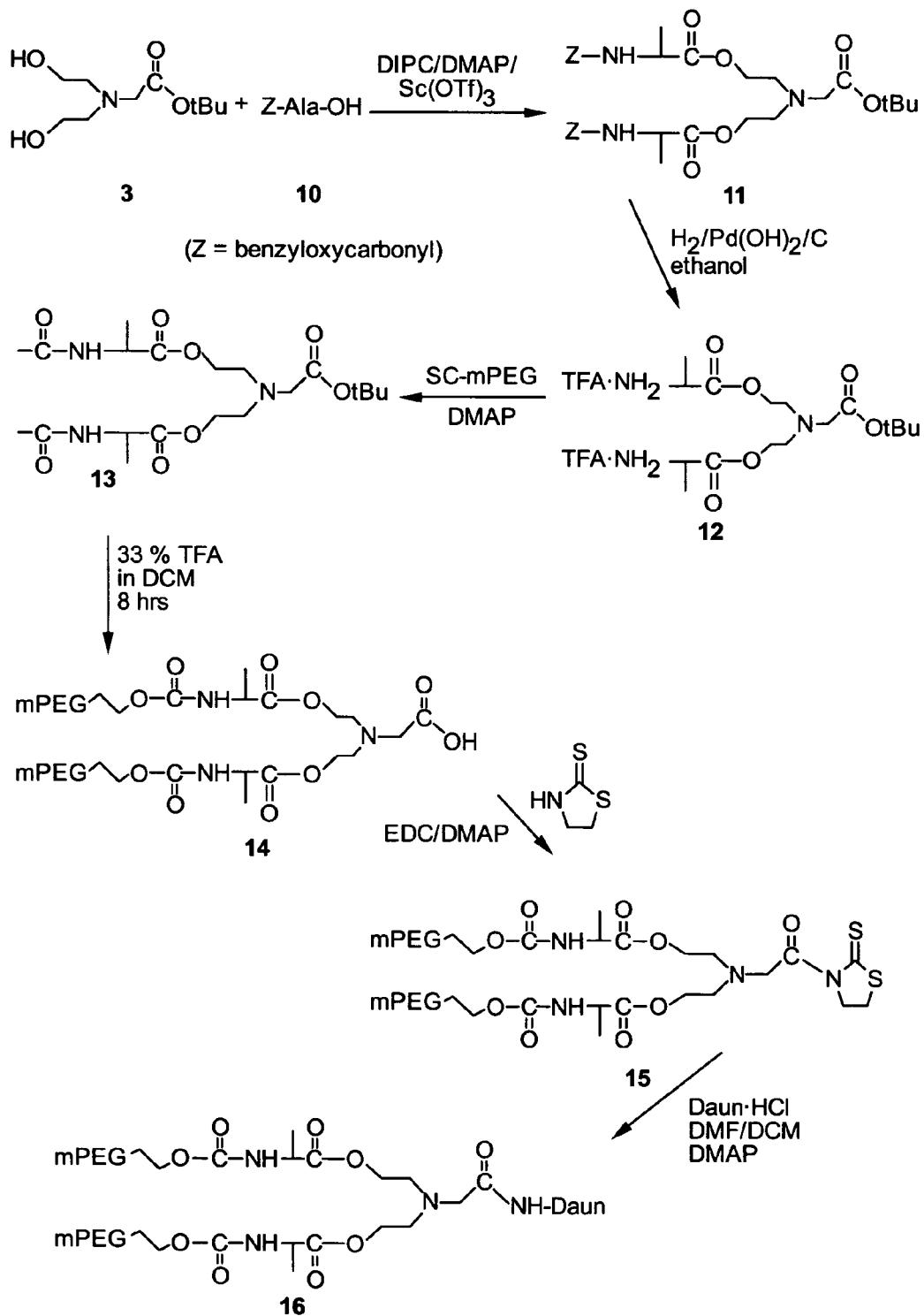
FIG. 2 provides reaction schemes corresponding to examples 8-13.
Figure 3:
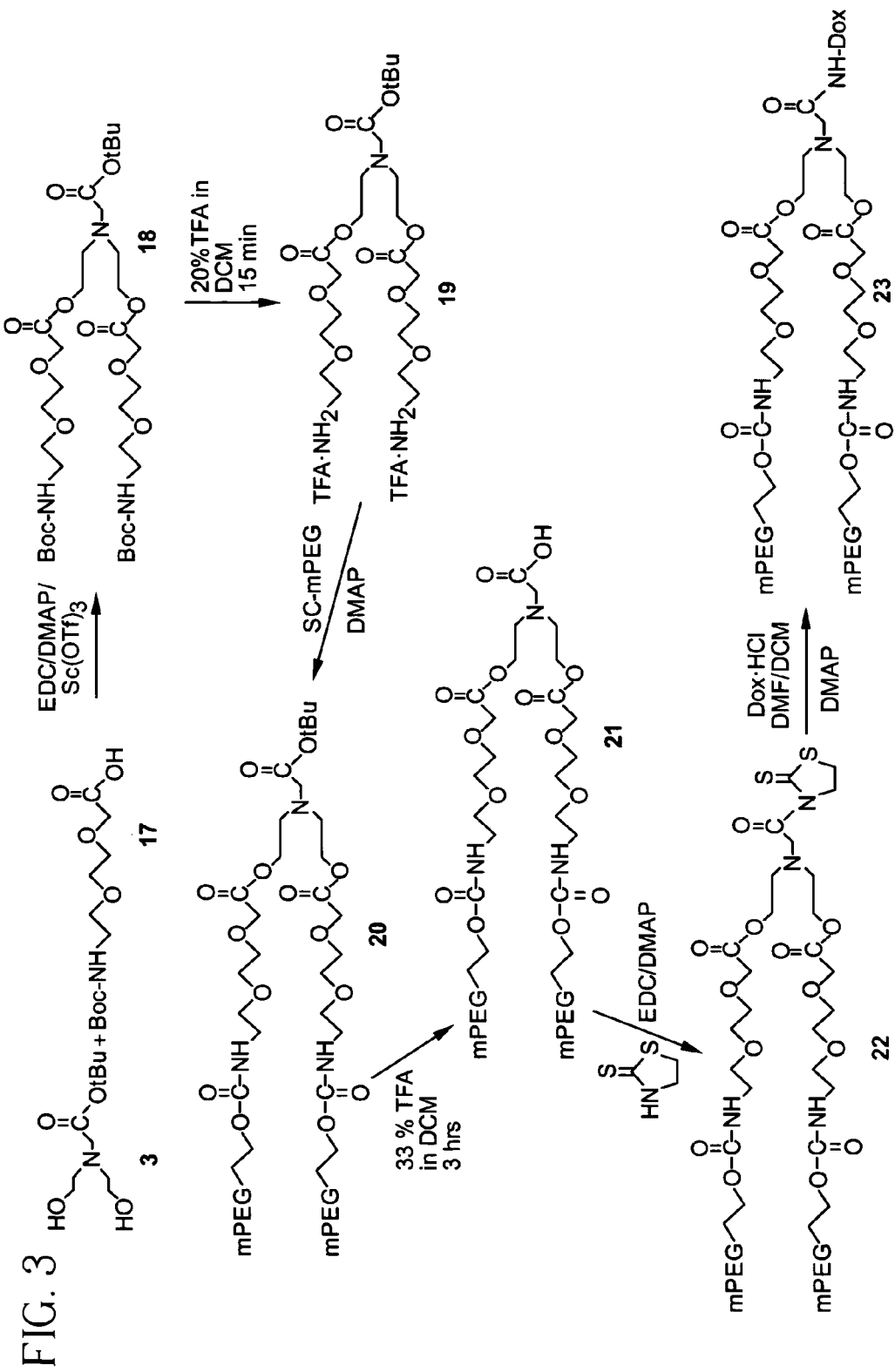
FIG. 3 provides reaction schemes corresponding to examples 14-20.
Figure 4:
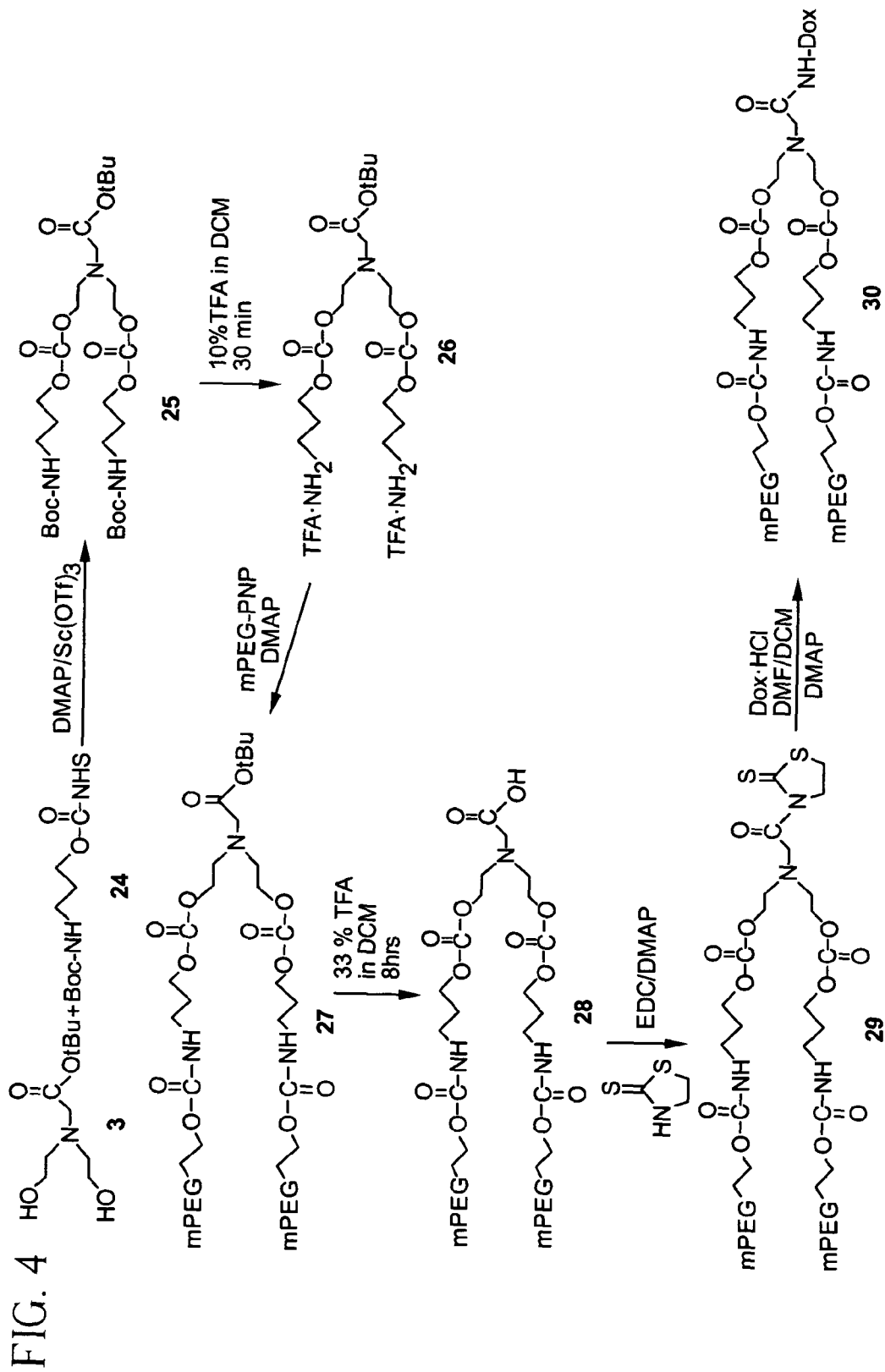
FIG. 4 provides reaction schemes corresponding to examples 21-27.
Figure 5:
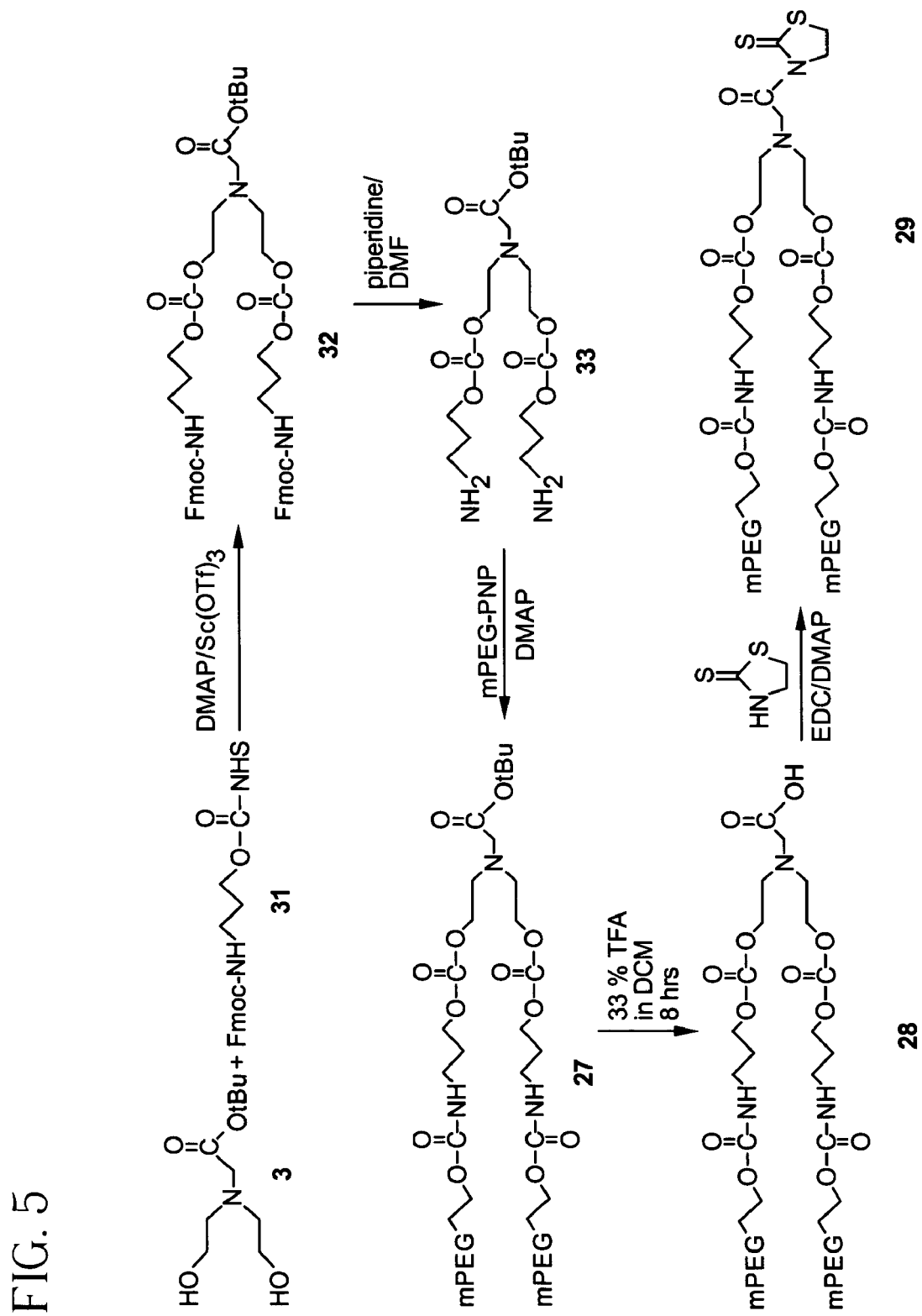
FIG. 5 provides reaction schemes corresponding to examples 28-29.
Figure 6:
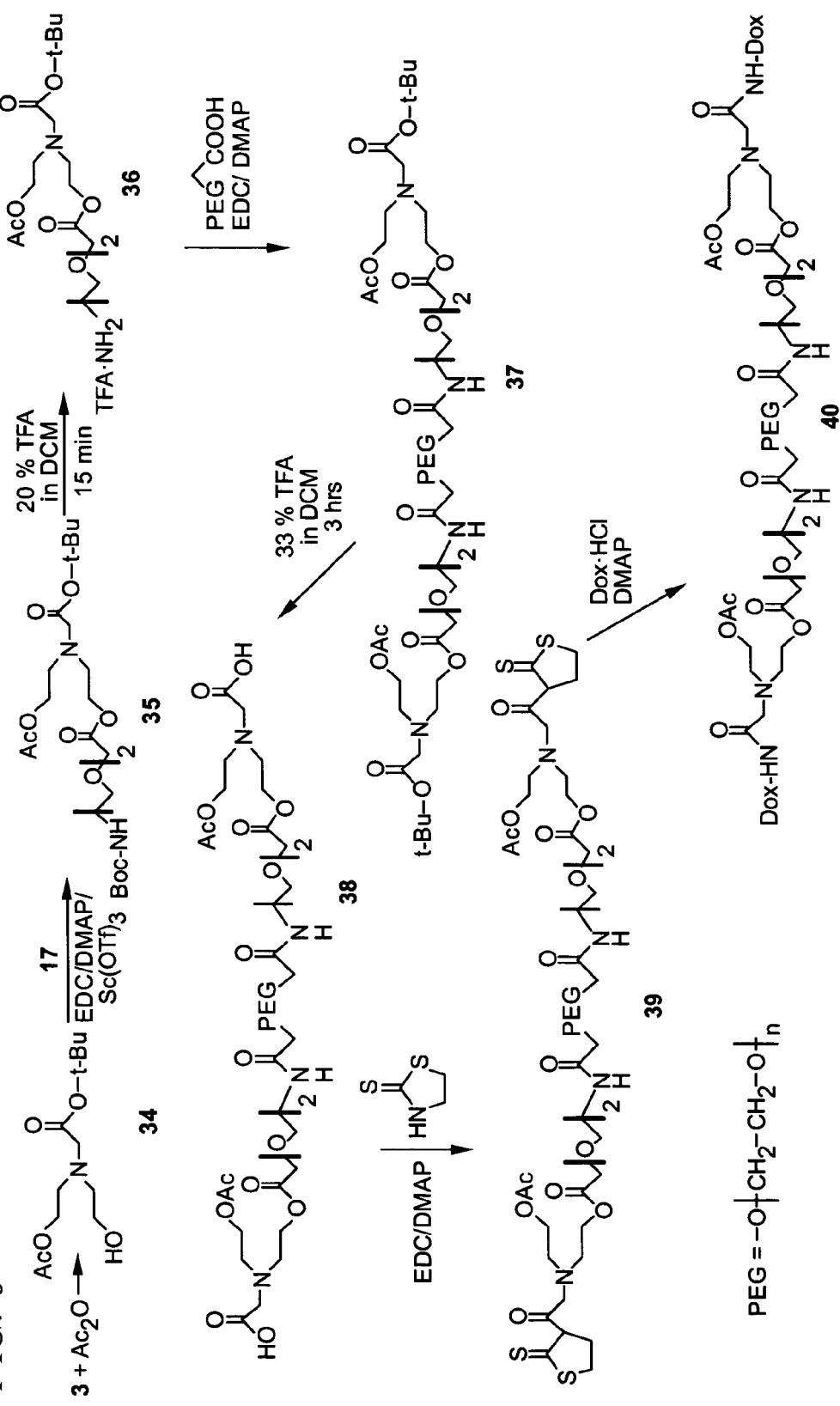
FIG. 6 provides reaction schemes corresponding to examples 30-36.
Figure 7:
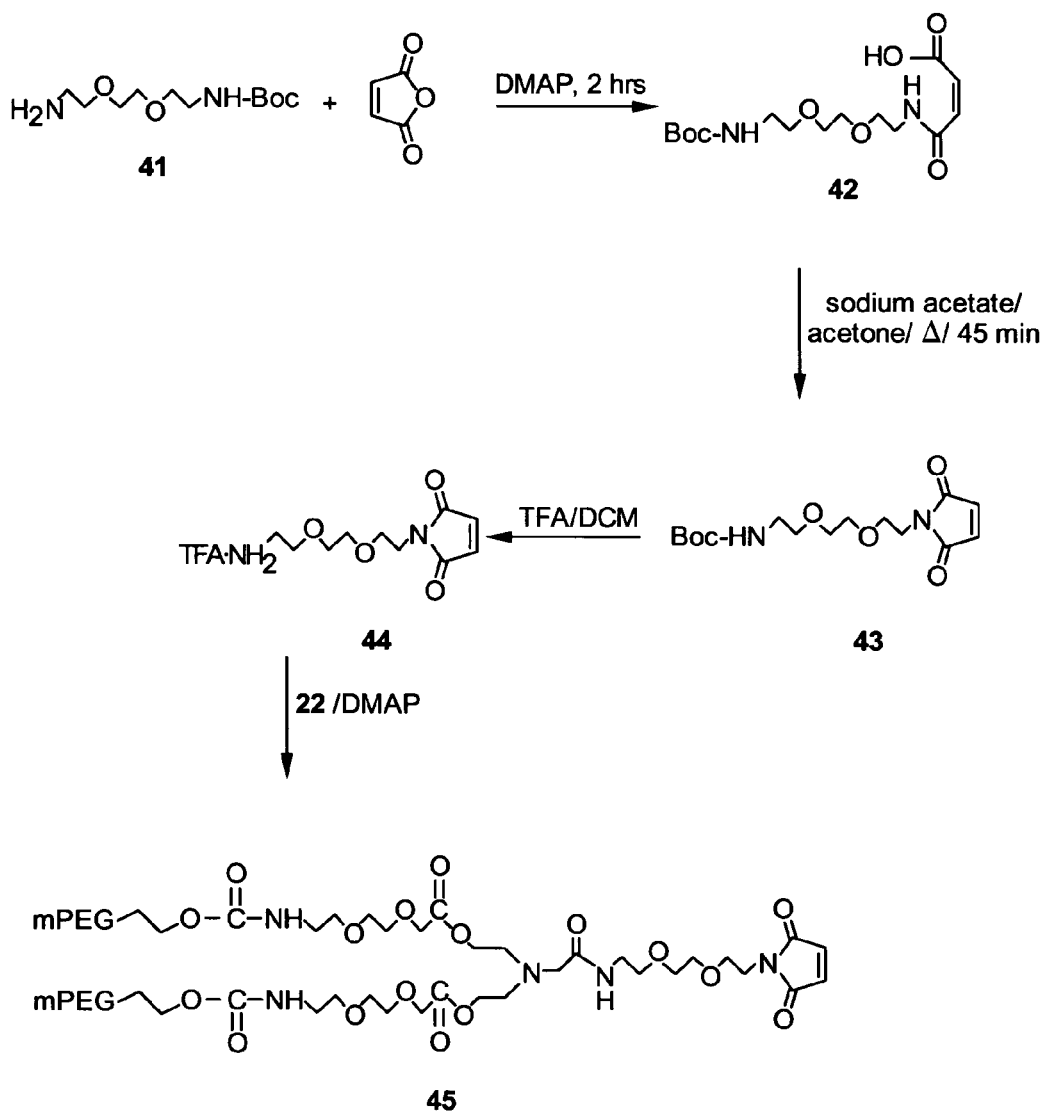
FIG. 7 provides reaction schemes corresponding to examples 37-40.
Figure 8:
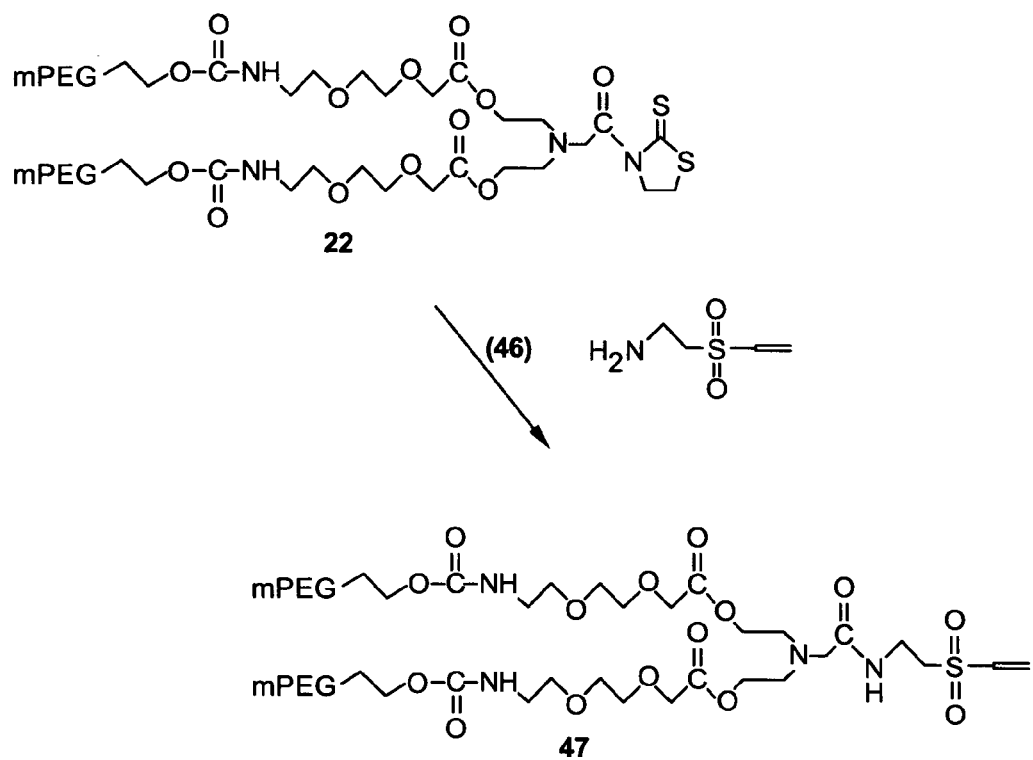
FIG. 8 provides reaction schemes corresponding to example 41.
Figure 9:
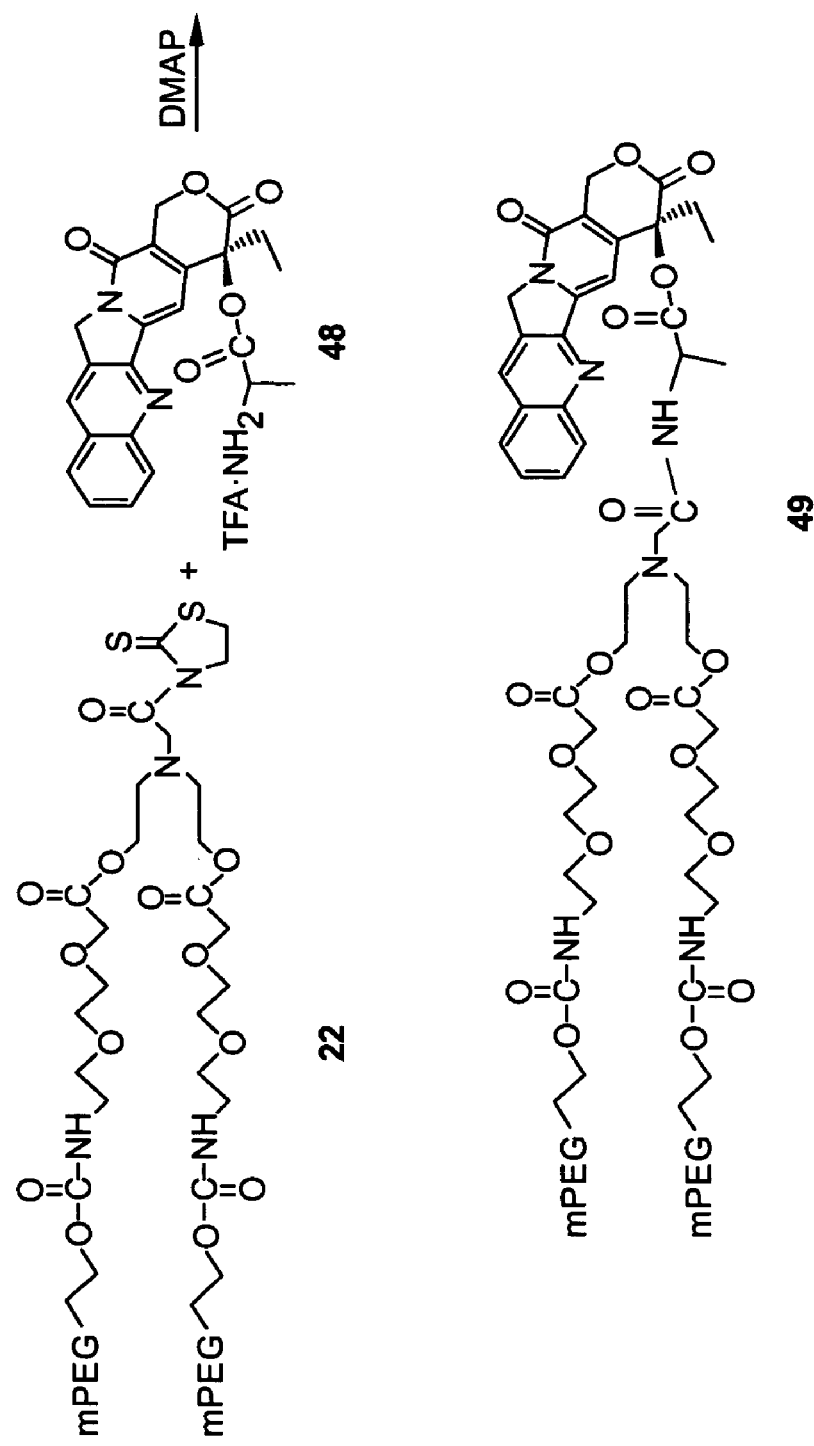
FIG. 9 provides reaction schemes corresponding to example 42.
Figure 10:
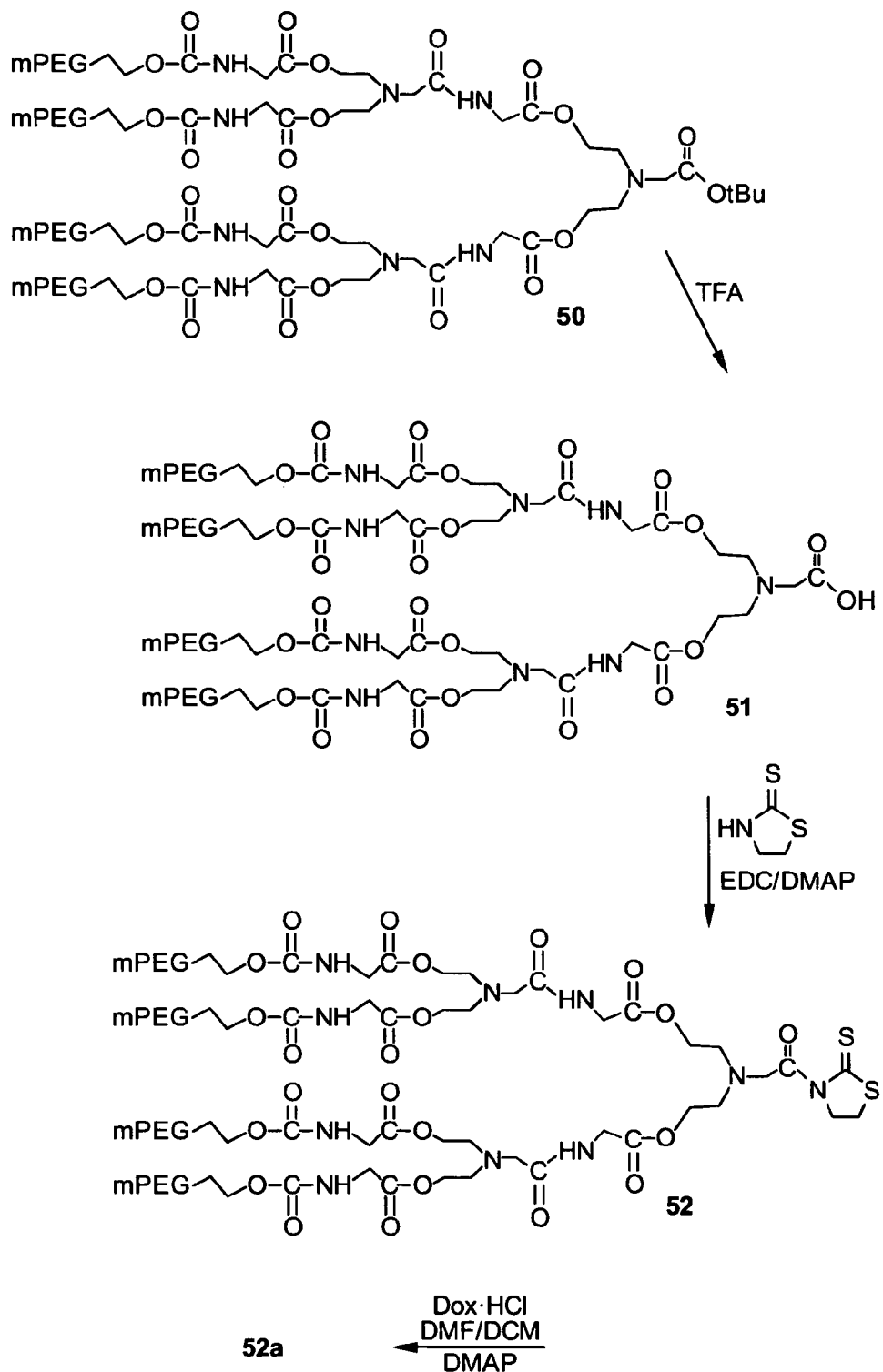
FIG. 10 provides reaction schemes corresponding to example 43.
Figure 11:
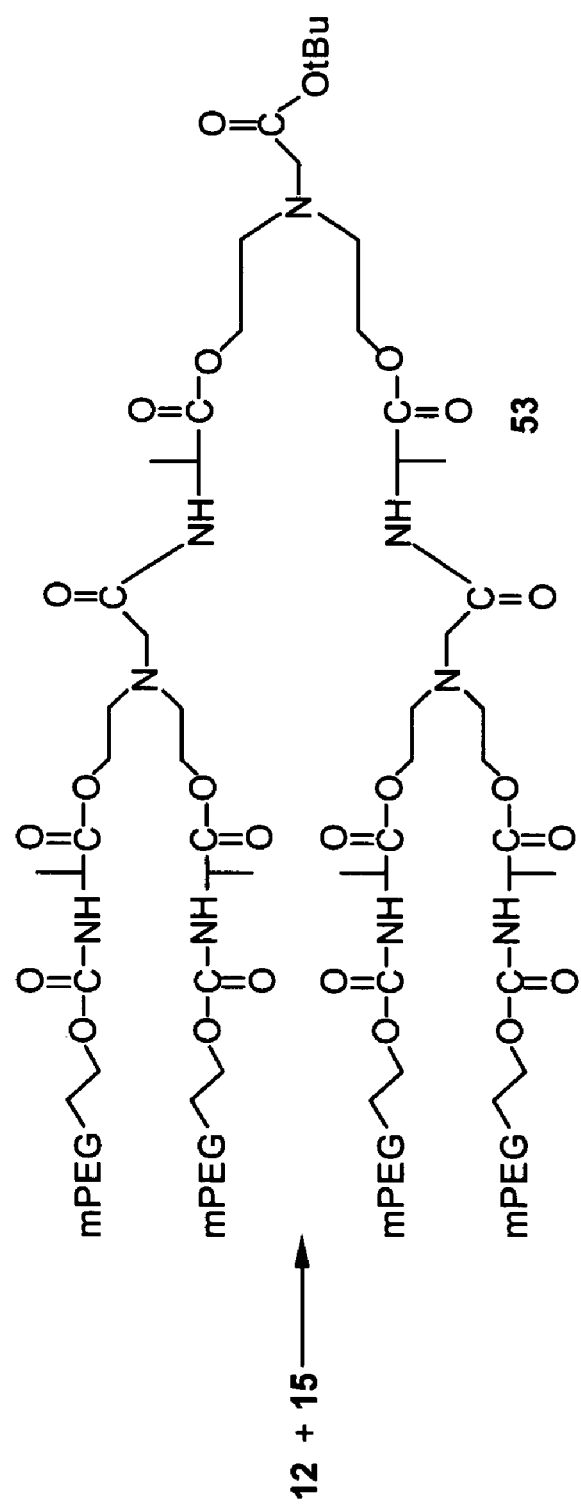
FIG. 11 provides reaction schemes corresponding to example 44.
Figure 12:
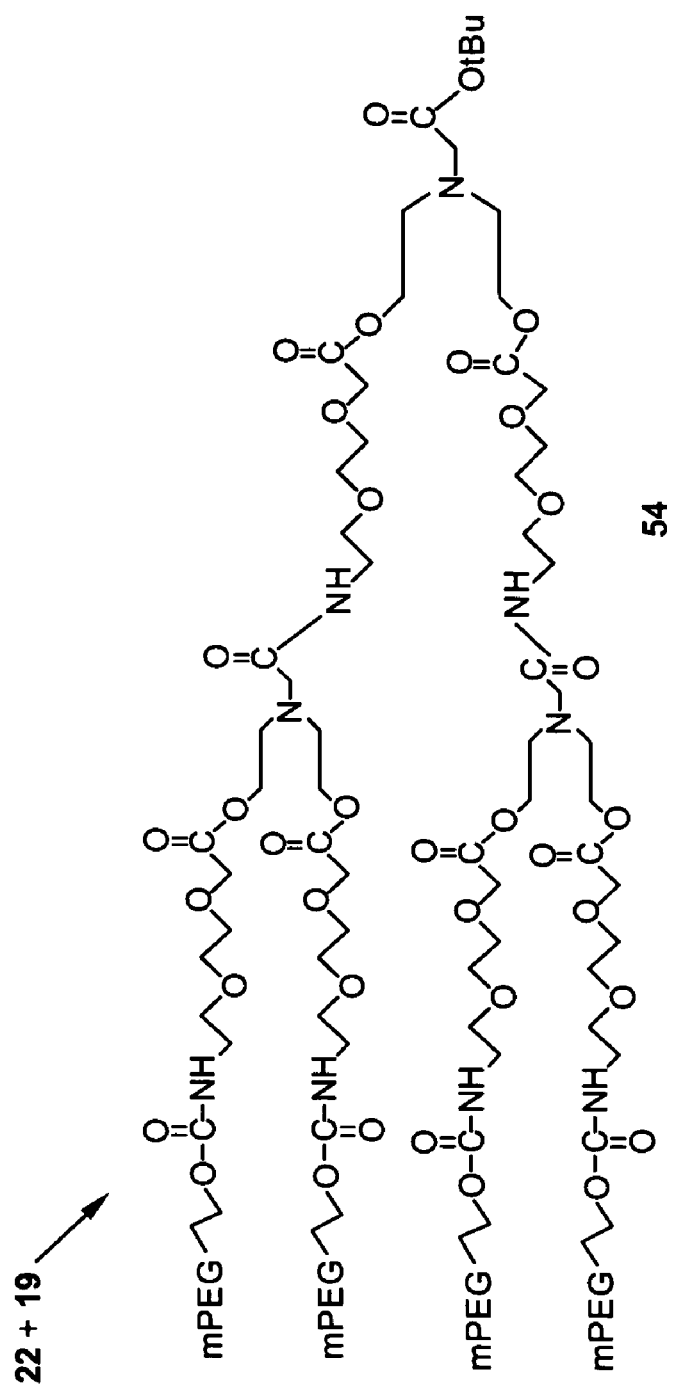
FIG. 12 provides reaction schemes corresponding to example 45.
Figure 13:
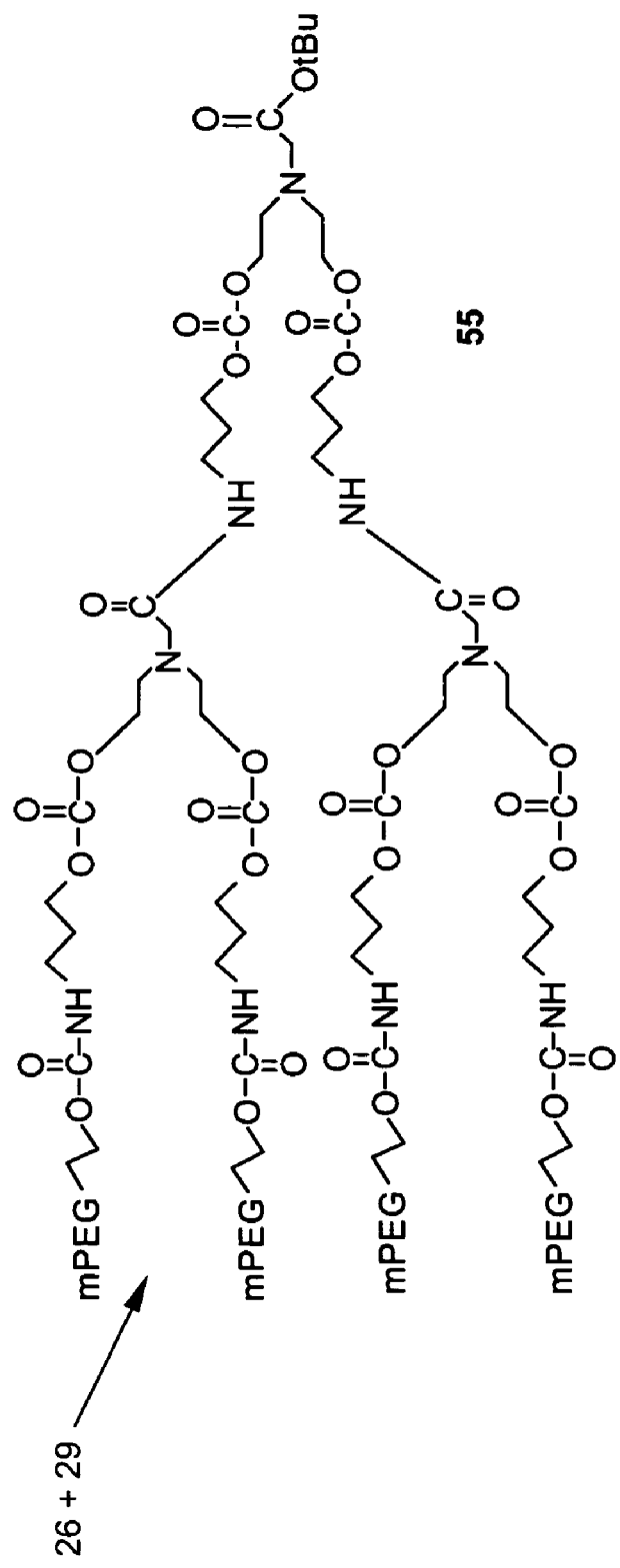
FIG. 13 provides reaction schemes corresponding to example 46.
Figure 14:
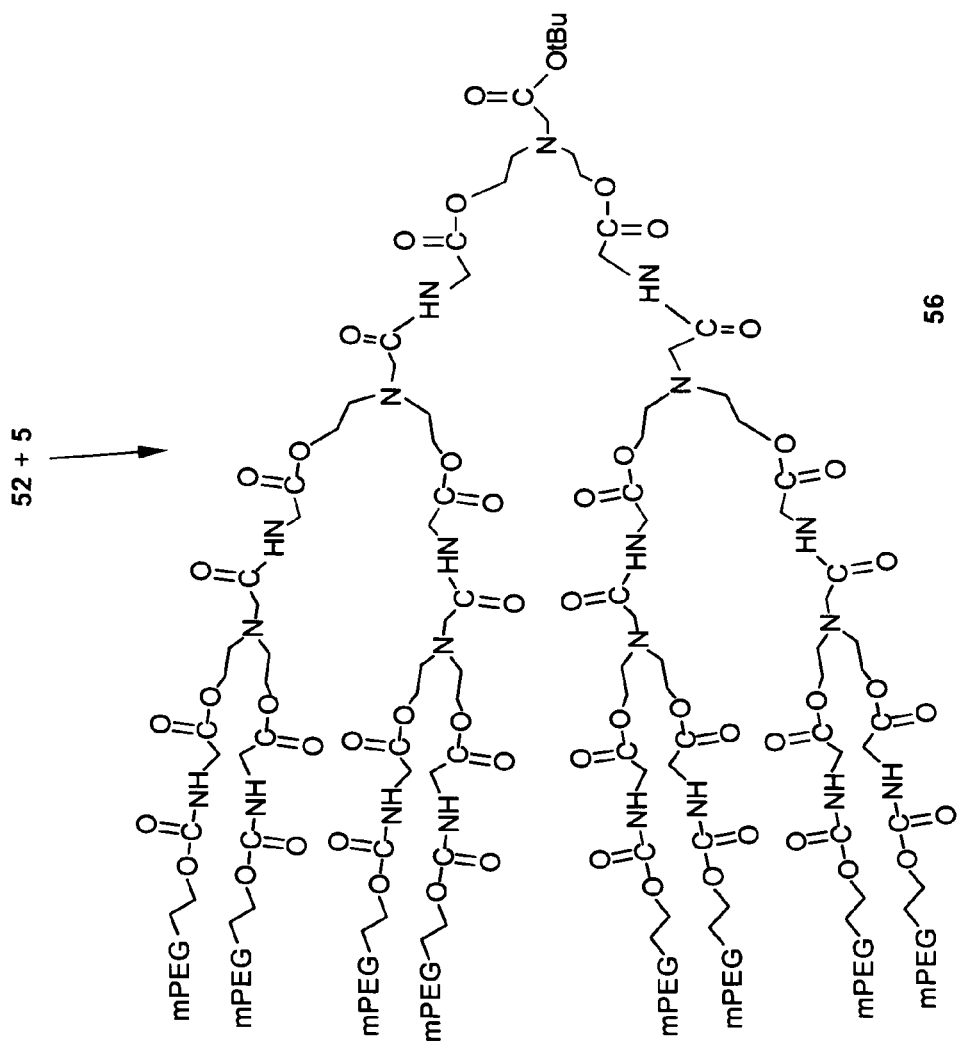
FIG. 14 provides reaction schemes corresponding to example 47.
Figure 15:
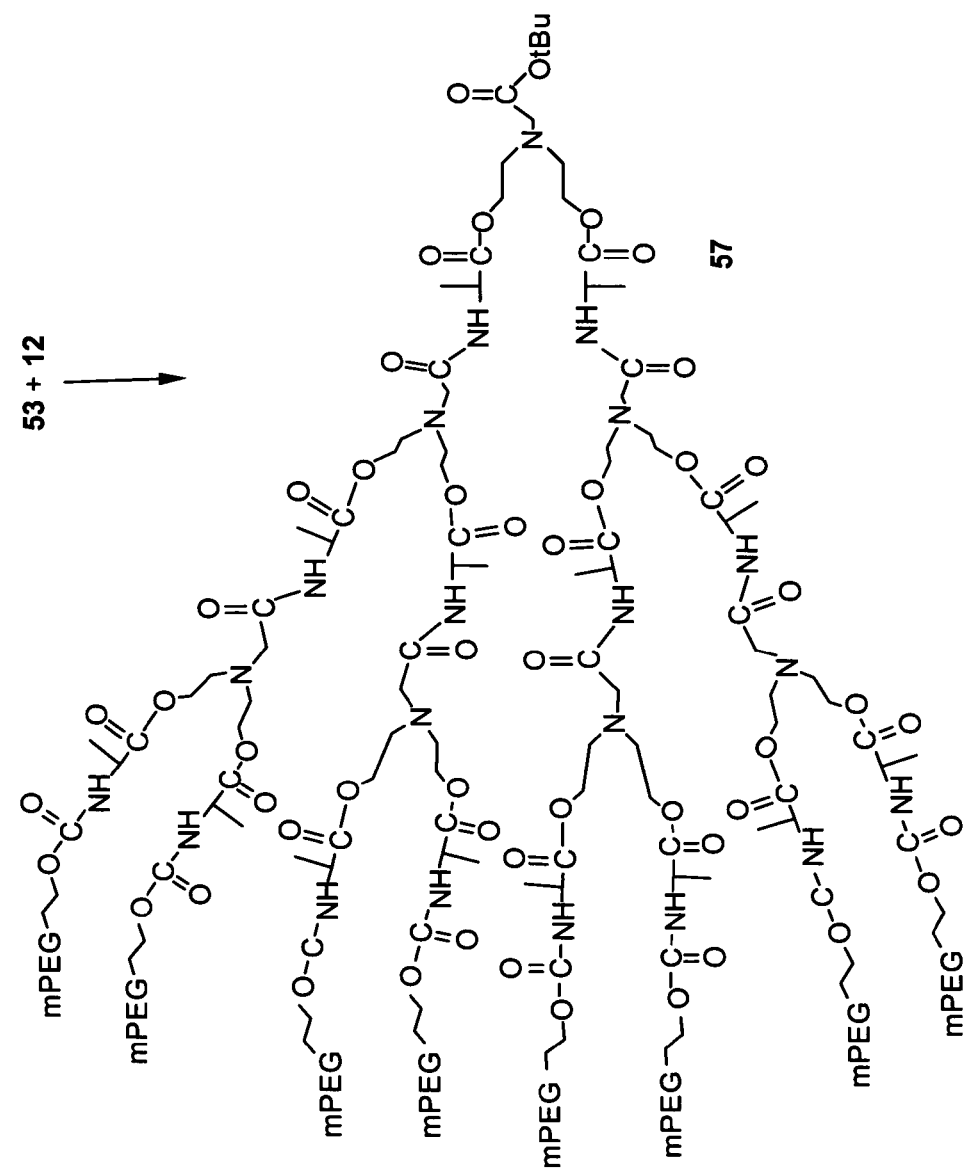
FIG. 15 provides reaction schemes corresponding to example 48.
Figure 16:
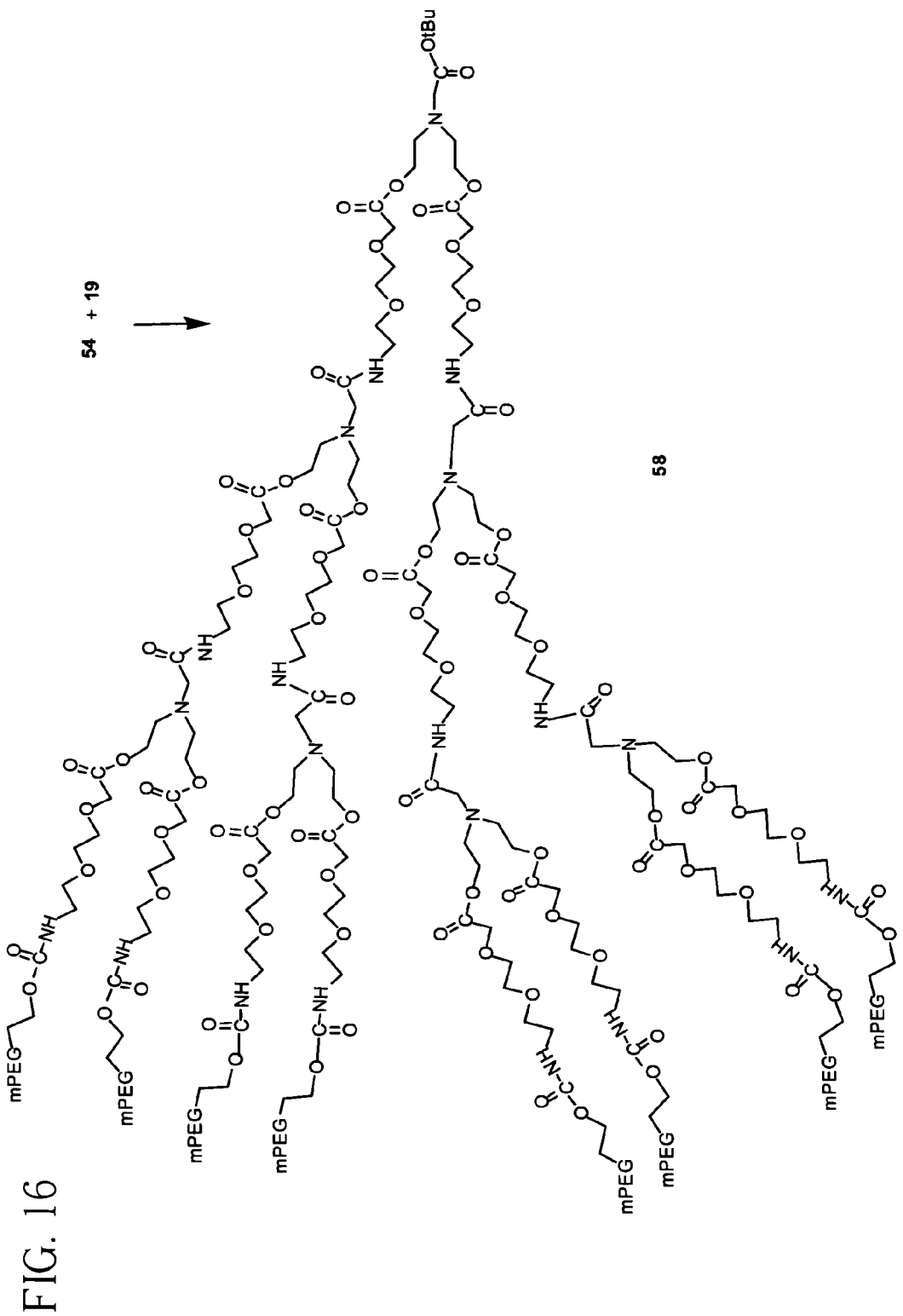
FIG. 16 provides reaction schemes corresponding to example 49.
Figure 17:
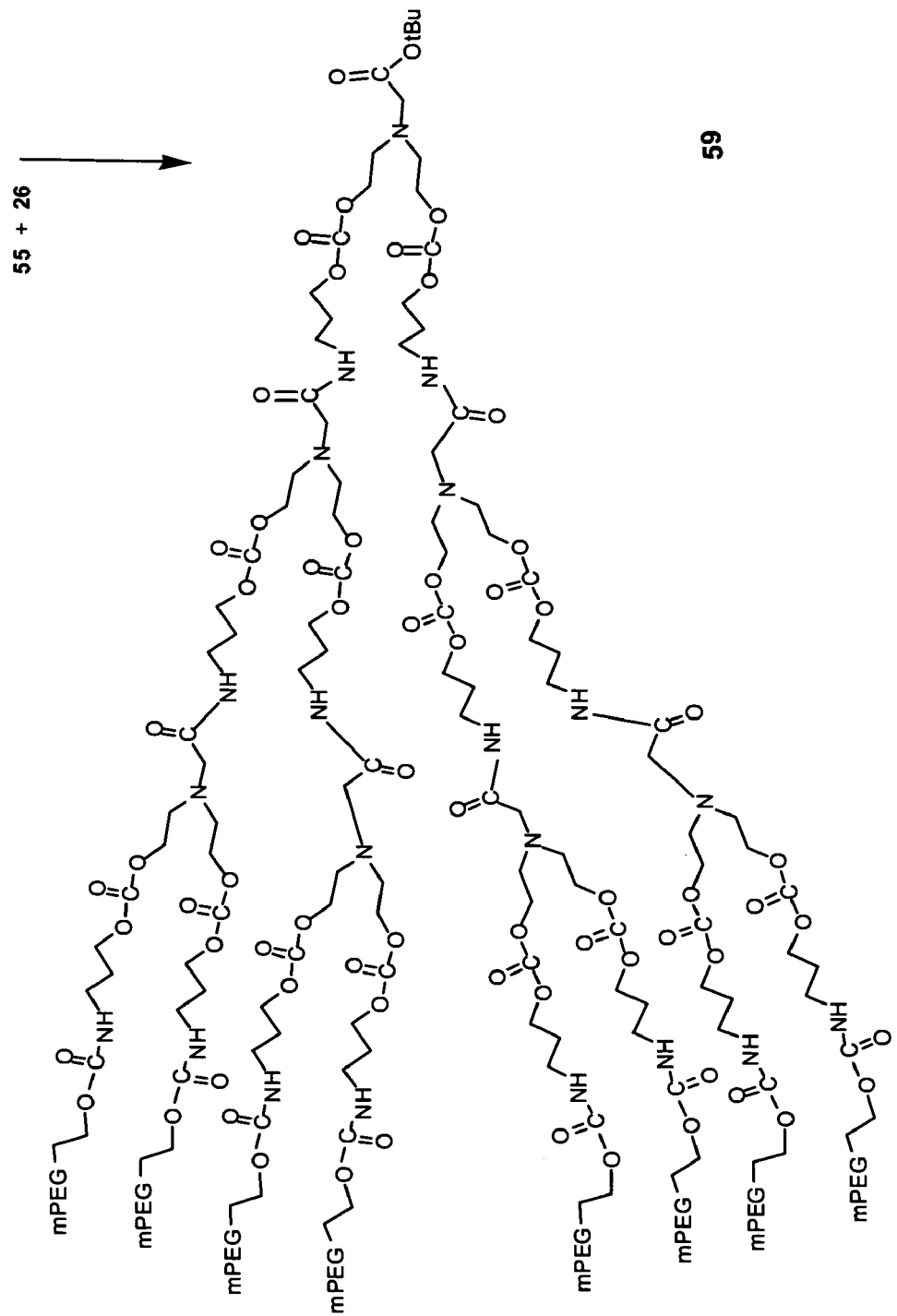
FIG. 17 provides reaction schemes corresponding to example 50.

In one embodiment of the invention, there are provided compounds of formula (I)

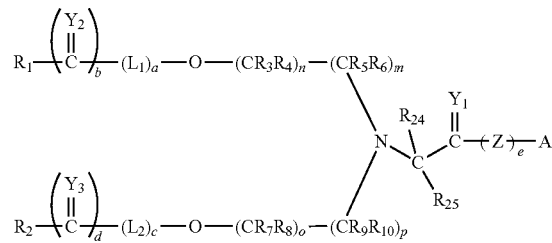

wherein:

$R_1$ and $R_2$ are independently selected from the group consisting of substantially non-antigenic polymer residues, $C_{1-6}$ alkyls, aralkyls, and terminal branching groups;

$Y_{1-3}$ are independently selected from among O, S or $NR_{11}$;

$L_1$ and $L_2$ are independently selected bifunctional linkers;

Z is selected from among moieties actively transported into a target cell, hydrophobic moieties, bifunctional linking moieties and combinations thereof $R_3$-$R_{11}$, $R_{24}$ and $R_{25}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

A is selected from among leaving groups, functional groups, residues of amine-containing agents such as biologically active proteins, peptides, chemotherapeutics, etc. and OH, a and c are each independently 0 or a positive integer;

b, d and e are independently 0 or 1; and m, n, o, and p are independently selected positive integers.

In certain preferred aspects of the invention, one or more of $R_1$ and $R_2$ include a substantially non-antigenic polymeric residue such as a polyethylene glycol (PEG) group. Optionally, $R_{1-2}$ include a capping group designated herein as J. Preferred J groups used for polymer capping include moieties such as OH, $NH_2$, SH, $CO_2H$, $C_{1-6}$ alkyl moieties, such as $CH_3$, and compounds of formulae (IIIa) and (IIIb):

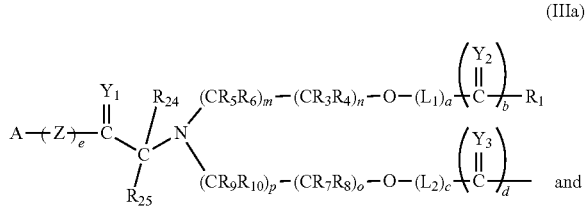

(IIIa)

and

-continued

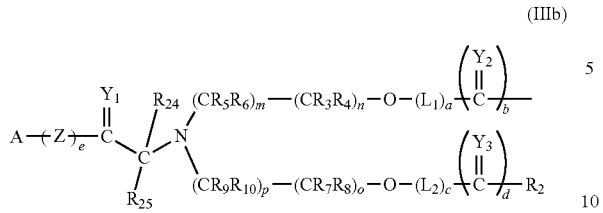
(IIIb)

where all variables are as previously defined.

With regard to the other variables which comprise the formulae of the present invention, the following are preferred in certain aspects of the invention:

in certain aspects, $R_1$ and $R_2$ are polyalkylene oxide residues, and more preferably polyethylene glycol residues;

in other aspects, $R_1$ and $R_2$ are bicine-based terminal branching groups described in more detail below to allow multiple polymer strand loading;

$R_3$-$R_{10}$, and $R_{24-25}$ are each hydrogen;

a, b, c, d, m, n, o and p preferably each 1;

e is preferably 0 or 1;

$L_1$ and $L_2$ are each preferably one of NRCH(CH$_3$)C(O)—, NHCH$_2$C(O)—, NH(CH$_2$CH$_2$O)$_2$CH$_2$C(O)—, or NH(CH)$_3$OC(O)—; and Z is

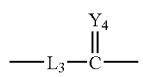

as defined above, or, alternatively Z comprises an amino acid residue, a peptide residue, a group which is actively transported into a target cell, hydrophobic or has combinations of such properties, such that when combined with biologically active A groups, prodrugs are formed which release from the bicine polymeric portion of formulae (I), (II), etc. See also commonly assigned U.S. Ser. No. 09/758,993, the contents of which are incorporated herein by reference.

B. Substantially Non-Antigenic Polymers

As stated above, $R_1$ and $R_2$ are preferably each water soluble polymer residues which are preferably substantially non-antigenic such as polyalkylene oxides (PAO's) and more preferably polyethylene glycols such as mPEG. For purposes of illustration and not limitation, the polyethylene glycol (PEG) residue portion of $R_1$ can be selected from among:

J-O—(CH$_2$CH$_2$O)$_x$—

J-O—(CH$_2$CH$_2$O)$_x$—CH$_2$C(O)—O—,

J-O—(CH$_2$CH$_2$O)$_x$—CH$_2$CH$_2$NR$_{12}$—,

J-O—(CH$_2$CH$_2$O)$_x$—CH$_2$CH$_2$SH—,

—OC(O)CH$_2$—O—(CH$_2$CH$_2$O)$_x$—CH$_2$C(O)—O—,

—NR$_{12}$CH$_2$CH$_2$—O—(CH$_2$CH$_2$O)$_x$—CH$_2$CH$_2$NR$_{12}$— and

—SHCH$_2$CH$_2$—O—(CH$_2$CH$_2$O)$_x$—CH$_2$CH$_2$SH—.

Similarly, for $R_2$, the PEG residue can be selected from among:

J-O—(CH$_2$CH$_2$O)$_x$—

J-O—(CH$_2$CH$_2$O)$_x$—CH$_2$C(O)—O—,

J-O—(CH$_2$CH$_2$O)$_x$—CH$_2$CH$_2$NR$_{13}$—,

J-O—(CH$_2$CH$_2$O)$_x$—CH$_2$CH$_2$SH—,

—OC(O)CH$_2$—O—(CH$_2$CH$_2$O)$_x$—CH$_2$C(O)—O—,

—NR$_{13}$CH$_2$CH$_2$—O—(CH$_2$CH$_2$O)$_x$—CH$_2$CH$_2$NR$_{13}$— and

—SHCH$_2$CH$_2$—O—(CH$_2$CH$_2$O)$_x$—CH$_2$CH$_2$SH—.

In each of the foregoing cases, x is the degree of polymerization, $R_{23-24}$ are individually selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy and J is a capping group as described above with regard to Formula II.

In one particularly preferred embodiment, $R_{1-2}$ are selected from among

CH$_3$—O—(CH$_2$CH$_2$O)$_x$—, CH$_3$—O—(CH$_2$CH$_2$O)$_x$—CH$_2$C(O)—O—,

CH$_3$—O—(CH$_2$CH$_2$O)$_x$—CH$_2$CH$_2$NH— and CH$_3$—O—(CH$_2$CH$_2$O)$_x$—CH$_2$CH$_2$SH—, where x is a positive integer, preferably selected so that the weight average molecular weight from about 2,000 to about 25,000 Da. In alternative aspects of the invention, the molecular weight of the polymer ranges from several hundred up to 40,000 Or greater, depending upon the needs of the artisan. PEG is generally represented by the structure:

—O—(CH$_2$CH$_2$O—)$_x$— and $R_1$ and $R_2$ preferably comprise residues of this formula.

The degree of polymerization for the polymer (x) can be from about 10 to about 2,300. This represents the number of repeating units in the polymer chain and is dependent on the molecular weight of the polymer. The (J) moiety is a capping group as defined herein, i.e. a group which is found on the terminal of the polymer and, in some aspects, can be selected from any of NH$_2$, OH, SH, CO$_2$H, $C_{1-6}$ alkyls or other PEG terminal activating groups, as such groups are understood by those of ordinary skill.

Also useful are polypropylene glycols, branched PEG derivatives such as those described in commonly-assigned U.S. Pat. No. 5,643,575 (the '575 patent), "star-PEG's" and multi-armed PEG's such as those described in Shearwater Corporation's 2001 catalog "Polyethylene Glycol and Derivatives for Biomedical Application". The disclosure of each of the foregoing is incorporated herein by reference. The branching afforded by the '575 patent allows secondary or tertiary branching from the bicine group as a way of increasing polymer loading on a biologically active molecule or enzyme from a single point of attachment. It will be understood that the water-soluble polymer can be functionalized for attachment to the bifunctional linkage groups if required without undue experimentation.

Although PAO's and PEG's can vary substantially in weight average molecular weight, preferably, $R_1$ and $R_2$ each have a weight average molecular weight of from about 2,000 to about 25,000 Da in most aspects of the invention.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In a further embodiment, and as an alternative to PAO-based polymers, $R_1$ and $R_2$ are each optionally selected from among one or more effectively non-antigenic materials such as dextran, polyvinyl alcohols, carbohydrate-based polymers, hydroxypropylmeth-acrylamide (HPMA), polyalkylene oxides, and/or copolymers thereof See also commonly-assigned U.S. Pat. No. 6,153,655, the contents of which are incorporated herein by reference. It will be understood by those of ordinary skill that the same type of activation is employed as described herein as for PAO's such as PEG. Those of ordinary skill in the art will further realize that the foregoing list is merely illustrative and that all polymeric materials having the qualities described herein are contemplated and that other polyalkylene oxide derivatives such as the polypropylene glycols, etc. are also contemplated.

The polymers of the present invention can also be copolymerized with bifunctional materials such as poly(alkylene glycol) diamines to form interpenetrating polymer networks suitable for use in permeable contact lenses, wound dressings, drug delivery devices and the like. The steric limitations and water solubility of such branching will be readily recognized by one of ordinary skill in the art. Preferably, however, the molecular weight of multiple branched polymers should not exceed 80,000 daltons.

C. Bifunctional Linker Groups $L_1$ and $L_2$

In many aspects of the invention, and formula (I) in particular, $L_1$ and/or $L_2$ are linking groups which facilitate attachment of the bicine derivative to the polymer strands, e.g. $R_1$ and/or $R_2$. The linkage provided can be either direct or through further coupling groups known to those of ordinary skill. Other $L_x$ groups are mentioned in the specification and they are understood to be selected from among the same groups as $L_1$. In this aspect of the invention, $L_1$ is preferably selected from among:

—NH(CH$_2$CH$_2$O)$_2$CH$_2$C(O)—

—NH(CH$_2$)$_3$OC(O)—

—(CH$_2$)$_t$C(O)—,

—C(O)NH(CH$_2$)$_t$C(O)—,

—NH(CH$_2$)$_t$C(O)—,

—NR$_{19}$(CH$_2$)$_t$(CH$_2$CH$_2$O)$_q$NHC(O)—

—(CH$_2$CH$_2$O)$_t$NHC(O)—

—O(CR$_{14}$R$_{15}$)$_t$NHC(O)—

—NR$_{19}$(CR$_{14}$R$_{15}$)$_q$C(O)NH(CR$_{16}$R$_{17}$)$_t$C(O)—

—O(CH$_2$)$_t$OC(O)—

—NR$_{19}$(CR$_{14}$R$_{15}$)$_t$C(O)—

—NR$_{19}$(CH$_2$)$_t$(CH$_2$CH$_2$O)$_q$NHC(O)—

—NR$_{19}$(CH$_2$CH$_2$O)$_t$—OC(O)—

—O(CR$_{14}$R$_{15}$)$_t$NHC(O)—

—O(CR$_{14}$R$_{15}$)$_t$OC(O)—

—(CH$_2$CH$_2$O)$_t$NHC(O)—

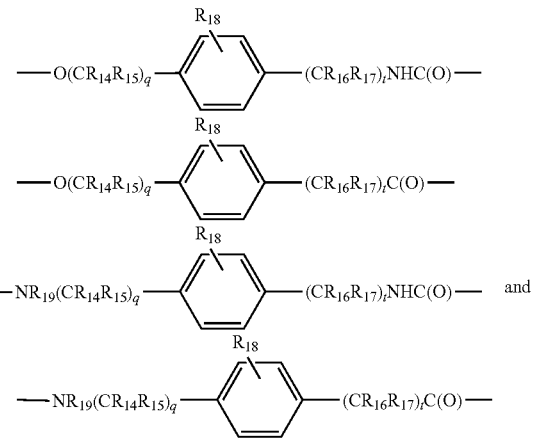

wherein $R_{14}$-$R_{17}$ and $R_{19}$ are independently selected from the group consisting of hydrogen, $C_{1-6}$ alkyls, $C_{3-9}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; and $R_{1-8}$ is selected from the group consisting of hydrogen, $C_{1-6}$ alkyls, $C_{3-9}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, NO$_2$, haloalkyl and halogen; and t and q are individually selected positive integers, preferably from about 1 to about 4.

Similarly, $L_2$ can be selected from among:

—NH(CH$_2$CH$_2$O)$_2$CH$_2$C(O)—

—NH(CH$_2$)$_3$OC(O)—

—(CH$_2$)$_v$C(O)—,

—C(O)(CH$_2$)$_v$NHC(O)—,

—NH(CH$_2$)$_v$C(O)—,

—NR$_{25}$(CH$_2$)$_v$(CH$_2$CH$_2$O)$_w$NHC(O)—

—(CH$_2$CH$_2$O)$_v$NHC(O)—,

—O(CR$_{20}$R$_{21}$)$_v$NHC(O)—,

—NR$_{25}$(CR$_{20}$R$_{21}$)$_w$(O)CNH(CR$_{22}$C$_{23}$)$_v$C(O)—

—O(CH$_2$)$_v$OC(O)—

—NR$_{25}$(CR$_{20}$R$_{21}$)$_v$C(O)—

—NR$_{25}$(CH$_2$)$_v$(CH$_2$CH$_2$O)$_w$NHC(O)—

—NR$_{25}$(CH$_2$CH$_2$O)$_v$—O—C(O)

—O(CR$_{20}$R$_{21}$)$_v$NHC(O)—

—O(CR$_{20}$R$_{21}$)$_v$OC(O)—

—(CH$_2$CH$_2$O)$_v$NHC(O)—

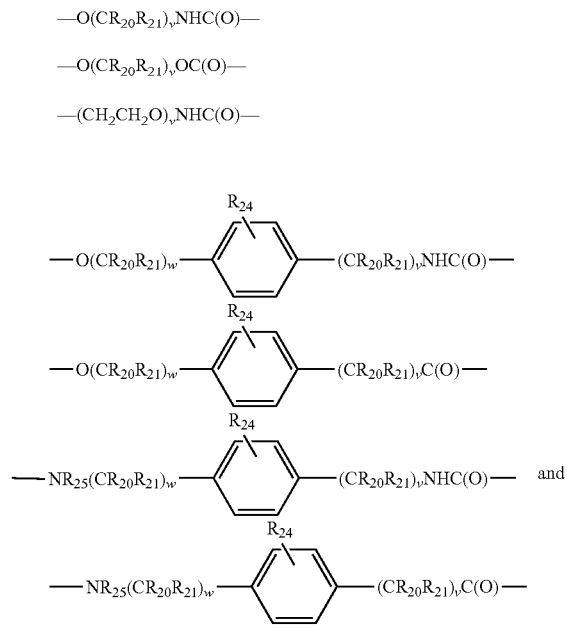

wherein R$_{20}$-R$_{23}$ and R$_{25}$ are independently selected from the group consisting of hydrogen, C$_{1-6}$ alkyls, C$_{3-19}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy and R$_{24}$ is selected from the group consisting of hydrogen, C$_{1-6}$ alkyls, C$_{3-19}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy, NO$_2$, haloalkyl and halogen; and v and w are individually selected positive integers, preferably from about 1 to about 4.

In other aspects of the invention, L$_1$ and/or L$_2$ can include an amino acid residue. The amino acid can be selected from any of the known naturally-occurring L-amino acids is, e.g., alanine, valine, leucine, isoleucine, glycine, serine, threonine, methionine, cysteine, phenylalanine, tyrosine, tryptophan, aspartic acid, glutamic acid, lysine, arginine, histidine, proline, and/or a combination thereof, to name but a few. When L$_1$ and/or L$_2$ include a peptide, the peptide ranges in size, for instance, from about 2 to about 10 amino acid residues. In one preferred embodiment, the peptide is Gly-Phe-Leu-. Alternatively, glycine can be added to the aforementioned tripeptide after leucine to form a 4 residue peptide.

The amino acid residues are preferably of the formula

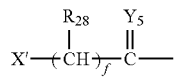

wherein X' is O, S or NR$_{26}$, Y$_5$ is O, S or NR$_{27}$, and R$_{26}$, R$_{27}$ and R$_{28}$ are independently selected from the same group as that which defines R$_3$ but each is preferably H or lower alkyl; and f is a positive integer from about 1 to about 10, and is preferably 1.

Derivatives and analogs of the naturally occurring amino acids, as well as various art-known non-naturally occurring amino acids (D or L), hydrophobic or non-hydrophobic, are also contemplated to be within the scope of the invention. Simply by way of example, amino acid analogs and derivates include: 2-aminoadipic acid, 3-amino-adipic acid, beta-alanine, beta-aminopropionic acid, 2-aminobutyric acid, 4-amino-butyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2-diaminopimelic acid, 2,3-diaminopropionic acid, n-ethylglycine, N-ethylasparagine, 3-hydroxyproline, 4-hydroxyproline, isodesmosine, allo-isoleucine, N-methylglycine, sarcosine, N-methylisoleucine, 6-N-methyl-lysine, N-methylvaline, norvaline, norleucine, ornithine, and others too numerous to mention, that are listed in 63 Fed. Reg., 29620, 29622, incorporated by reference herein.

Short peptides are, for example, peptides ranging from 2 to about 10, or more, amino acid residues, as mentioned supra.

D. Z Moieties and their Function

In one aspect of the invention Z is L$_3$-C(=Y$_4$) wherein L$_3$ is a bifunctional linker selected from among the group which defines L$_1$ and L$_2$ and Y$_4$ is selected from among the same groups as that which defines Y$_{1-3}$. In this aspect of the invention, the Z group servers as the linkage between the A groups and the remainder of the bicine transport form.

In other aspects of the invention, Z is a moiety that is actively transported into a target cell, a hydrophobic moiety, and combinations thereof. Although Z is preferably monovalent, Z can optionally be bivalent or multivalent so to allow attachment of more than one A group to the bicine-based polymer. In order to achieve the active transport, Z can include an amino acid or peptide residue, such as any of those described above with regard to L$_1$ and L$_2$, a sugar residue, a fatty acid residue, a C$_{6-8}$ alkyl, a substituted aryl, a heteroaryl, —C(=O), —C(=S) or —C(=NR$_{29}$), wherein R$_{29}$ is H, lower alkyl, etc.

This aspect of the invention is broadly based upon the principle that biologically active materials suitable for incorporation into the bicine-polymer-based prodrug conjugates may themselves be substances/compounds which are not active after hydrolytic release from the bicine-linked composition, but which will become active after undergoing a further chemical process/reaction. With this embodiment, a therapeutic or diagnostic agent, peptide, polypeptide, etc. that is delivered to the bloodstream by the bicine-based polymer system, will remain inactive until entering or being actively transported into a target cell of interest, whereupon it is activated by intracellular chemistry, e.g., by an enzyme or enzyme system present in that tissue or cell.

The prodrugs of this aspect of the invention are prepared so that in vivo hydrolysis of the bicine-polymer-based conjugate cleaves the conjugate so as to release the active biological material (designated A herein) into extracellular fluid, while still linked to the Z moiety. The biologically active materials in this aspect of the invention are preferably, but not exclusively, small molecule therapeutic and/or diagnostic agents. For example, one potential Z-A combination is leucine-doxorubacin, another is amino acid-linked camptothecin or paclitaxel and the tissue to be treated is tumor tissue.

Without intending to be bound by any theory or hypothesis as to how the invention might operate, it is believed that, depending upon the additional moiety selected as a transport enhancer, the rate of transport of a biologically active material into tumor cells is by the delivery of a biologically active material into extracellular tissue pace, e.g. of a tissue exhibiting an EPR effect, in a protected and/or transport-enhanced form.

In a further still option, the transport enhancer (Z) is selected from among known substrates for a cell membrane transport system. Simply by way of example, cells are known to actively transport certain nutrients and endocrine factors, and the like, and such nutrients, or analogs thereof, are readily employed to enhance active transport of a biologically effective material into target cells. Examples of these nutrients include amino acid residues, peptides, e.g., short peptides ranging in size from about 2 to about 10 residues or more, simple sugars and fatty acids, endocrine factors, and the like.

Short peptides are, for example, peptides ranging from 2 to about 10, or more, amino acid residues, as mentioned supra. In this embodiment of the invention, it is believed that such peptide transport enhancers need not be hydrophobic, but are thought to function in other ways to enhance uptake and/or to protect the linked small molecule agents from premature hydrolysis in the general bloodstream. For instance, peptide transport enhancers, and other transport enhancers of similar molecular weight ranges, are thought to sterically hinder cleavage from the biologically active agent by plasma-based hydrolytic enzymes, but are then cleaved within a target cell by various peptides and/or proteases, such as cathepsins.

In certain preferred aspects Z is a hydrophobic moiety. Without meaning to be bound to any theory or hypothesis as to how hydrophobicity contributes to efficacy, it is believed that a hydrophobic moiety inhibits the extracellular cleavage of the transport enhancer away from the active biological agent, by inhibiting the attack of hydrolytic enzymes, etc. present in the extracellular tissue space, e.g., in the plasma. Thus, some preferred transport enhancers include, e.g., hydrophobic amino acids such as alanine, valine, leucine, isoleucine, methionine, proline, phenylalanine, tyrosine, and tryptophane, as well as non-naturally occurring derivatives and analogs thereof, as mentioned supra.

In a further option, the transport enhancer is a hydrophobic organic moiety. Simply by way of example, the organic moiety is a $C_{6-18}$, or larger, alkyl, aryl or heteroaryl-substituted or nonsubstituted. The organic moiety transport enhancer is also contemplated to encompass and include organic functional groups including, e.g., —C(=S) and/or —C(=O).

E. Formula (I) A Groups

1. Leaving Groups

In those aspects where A is a leaving group, suitable moieties include, without limitation, groups such as N-hydroxybenzotriazolyl, halogen, N-hydroxyphthalimidyl, p-nitrophenoxy, imidazolyl, N-hydroxysuccinimidyl; thiazolidinyl thione, O-acyl ureas or

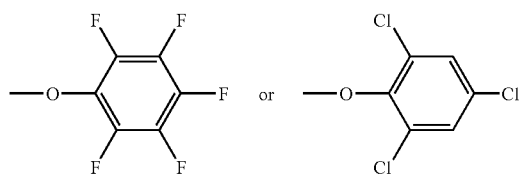

other suitable leaving groups will be apparent to those of ordinary skill.

For purposes of the present invention, leaving groups are to be understood as those groups which are capable of reacting with a nucleophile found on the desired target, i.e. a biologically active moiety, a bifunctional spacer, intermediate, etc. The targets thus contain a group for displacement, such as $NH_2$ groups found on proteins, peptides, enzymes, naturally or chemically synthesized therapeutic molecules such as doxorubicin, spacers such as mono-protected diamines such compound 42.

The compounds of the present invention can also include a spacer group between the bicine group and the leaving group or attached target (drug) if desired. The spacer moiety may be a heteroalkyl, alkoxy, alkyl containing up to 18 carbon atoms or even an additional polymer chain. The spacer moieties can be added using standard synthesis techniques. It is to be understood that those moieties selected for (A) can also react with other moieties besides biologically active nucleophiles.

2. Functional Groups

A can also be a functional groups. Non-limiting examples of such functional groups include maleimidyl, vinyl, residues of sulfone, hydroxy, amino, carboxy, mercapto, hydrazide, carbazate and the like which can be attached to the bicine portion through an amine-containing spacer. Once attached to the bicine portion, the functional group, (e.g. maleimide), can be used to attach the bicine-polymer to a target such as the cysteine residue of a polypeptide, amino acid or peptide spacer, etc.

3. Residues of Amine-Containing Compounds

In some aspects of the invention, A is a residue of an amine-containing compound. A non-limiting list of such suitable compounds includes residues of organic compounds, enzymes, proteins, polypeptides, etc. Organic compounds include, without limitation, moieties such as anthracycline compounds including daunorubicin, doxorubicin; p-aminoaniline mustard, melphalan, Ara-C (cytosine arabinoside) and related anti-metabolite compounds, e.g., gemcitabine, etc. Alternatively, A can be a residue of an amine-containing cardiovascular agent, anti-neoplastic, anti-infective, anti-fungal such as nystatin and amphotericin B, anti-anxiety agent, gastrointestinal agent, central nervous system-activating agent, analgesic, fertility agent, contraceptive agent, anti-inflammatory agent, steroidal agent, agent, etc.

In addition to the foregoing, A can also be a residue of an enzyme, protein, polypeptide, etc. Suitable proteins, polypeptides, enzymes, peptides and the like having at least one available group for polymer attachment, e.g. an ε-amino, cysteine, thio, N-terminal amino, include materials which have physiological or pharmacological activities as well as those which are able to catalyze reactions in organic solvents. The only other requirement of the amine-containing materials is that they maintain at least some portion of the activity associated with the unmodified protein, enzyme, peptide, etc. either after attachment to the polymeric transport or, if relevant, after the parent compound has been hydrolyzed and released.

Proteins, polypeptides and peptides of interest include, but are not limited to, hemoglobin, serum proteins such as blood factors including Factors VII, VIII, and IX; immunoglobulins, cytokines such as interleukins, i.e. IL-1 through IL-13, etc., α, β, and γ-interferons, colony stimulating factors including granulocyte colony stimulating factors, platelet derived growth factors and phospholipase-activating protein (PLAP). Other proteins of general biological or therapeutic interest include insulin, plant proteins such as lectins and ricins, tumor necrosis factors and related proteins, growth factors such as transforming growth factors, such as TGF α's or TGF β's and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

Some proteins such as the interleukins, interferons and colony stimulating factors also exist in non-glycosylated form, usually as a result of using recombinant techniques. The non-glycosylated versions are also among the proteins of the present invention.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catalases, chymotrypsin, lipases, uricases, adenosine diphosphatase, tyrosinases and bilirubin oxidase. Carbohydrate-specific enzymes of interest include glucose oxidases, glucodases, galactosidases, glucocerebrosidases, glucouronidases, etc.

Also included herein is any portion of a biological polymer demonstrating in vivo bioactivity. This includes amino acid sequences, nucleic acids (DNA, RNA), peptide nucleic acids (PNA), oligonucleotides, antibody fragments, single chain binding proteins, see, for example U.S. Pat. No. 4,946,778, disclosure of which is incorporated herein by reference, binding molecules including fusions of antibodies or fragments, polyclonal antibodies, monoclonal antibodies and catalytic antibodies.

The proteins or portions thereof can be prepared or isolated by using techniques known to those of ordinary skill in the art such as tissue culture, extraction from animal sources, or by recombinant DNA methodologies. Transgenic sources of the proteins, polypeptides, amino acid sequences and the like are also contemplated. Such materials are obtained from transgenic animals, i.e., mice, pigs, cows, etc., wherein the proteins are expressed in milk, blood or tissues. Transgenic insects and baculovirus expression systems are also contemplated as sources. Moreover, mutant versions of proteins, such as mutant interferons are also within the scope of the invention.

Other proteins of interest are allergen proteins such as ragweed, Antigen E, honeybee venom, mite allergen, and the like. The foregoing is illustrative of the proteins which are suitable for the present invention. It is to be understood that those proteins, as defined herein, not specifically mentioned but having an available amino group are also intended and are within the scope of the present invention.

In a preferred aspect of the invention, the amino-containing compound is a biologically active compound that is suitable for medicinal or diagnostic use in the treatment of animals, e.g., mammals, including humans, for conditions for which such treatment is desired. The foregoing list is meant to be illustrative and not limiting for the compounds which can be modified. Those of ordinary skill will realize that other such compounds/compositions can be similarly modified without undue experimentation. It is to be understood that those biologically active materials not specifically mentioned but having suitable attachment groups are also intended and are within the scope of the present invention.

F. Synthesis of Bicine Linked Polymers

Synthesis of specific bicine-based polymer compounds is set forth in the Examples. Turning now to FIG. 1 for the purpose of illustration, one preferred method includes:

1) synthesizing an acid protected bicine such as

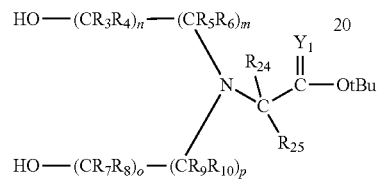

where tBu is a protecting group and all other variables are the same as previously set forth for formula (I)

2) attaching a blocked bifunctional spacer to each hydroxyl of the bicine molecule, 3) deprotecting the resultant intermediate and reacting it with an activated polymer such as PNP-PEG or SC-PEG under basic coupling conditions, 4) deprotecting the blocked acid and thereafter activating the acid with a suitable activating group such as thiazolidinyl thione, under coupling conditions.

It will be understood that other art recognized protecting groups can be used in place of t-Bu. The thus activated PEG or polymer bicine derivative is now capable of reacting with and conjugating to a drug, peptide, spacer, etc.

A non-limiting list of suitable coupling agents include 1,3-diisopropyl-carbodiimide (DIPC), any suitable dialkyl carbodiimide, 2-halo-1-alkyl-pyridinium halides (Mukaiyama reagents), 1-(3-dimethylaminopropyl)-3-ethyl carbodiimide (EDC), propane phosphonic acid cyclic anhydride (PPACA) and phenyl dichlorophosphates, etc. which are available, for example from commercial sources such as Sigma-Aldrich Chemical, or synthesized using known techniques.

Preferably the substituents are reacted in an inert solvent such as tetrahydrofuran (THF), acetonitrile ($CH_3CN$), methylene chloride (DCM), chloroform ($CHCl_3$), dimethyl formamide (DMF) or mixtures thereof. Suitable bases include dimethylaminopyridine (DMAP), diisopropylethylamine, pyridine, triethylamine, KOH, potassium t-butoxide and NaOH etc. The reactions are usually carried out at a temperature of from about 0° C. up to about 22° C. (room temperature).

More specifically, one method of forming the activated bicine derivatives includes 1) forming Bis N-2-hydroxyethyl glycine with t-butyl ester to give the intermediate:

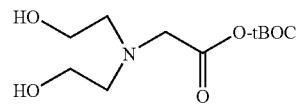

2) conjugating the N-hydroxy ethyl groups with protected amino acids or other protected linkers ($L_1$) to yield further intermediates:

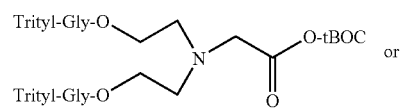

or

-continued
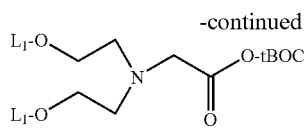
3) next, the bifunctional spacers are deprotected and the intermediate undergoes PEGylation, and
4) the remaining blocking group is deprotected and the bicine derivative is activated.
Regardless of the route selected, some of the preferred compounds which result from the synthetic techniques described herein include:
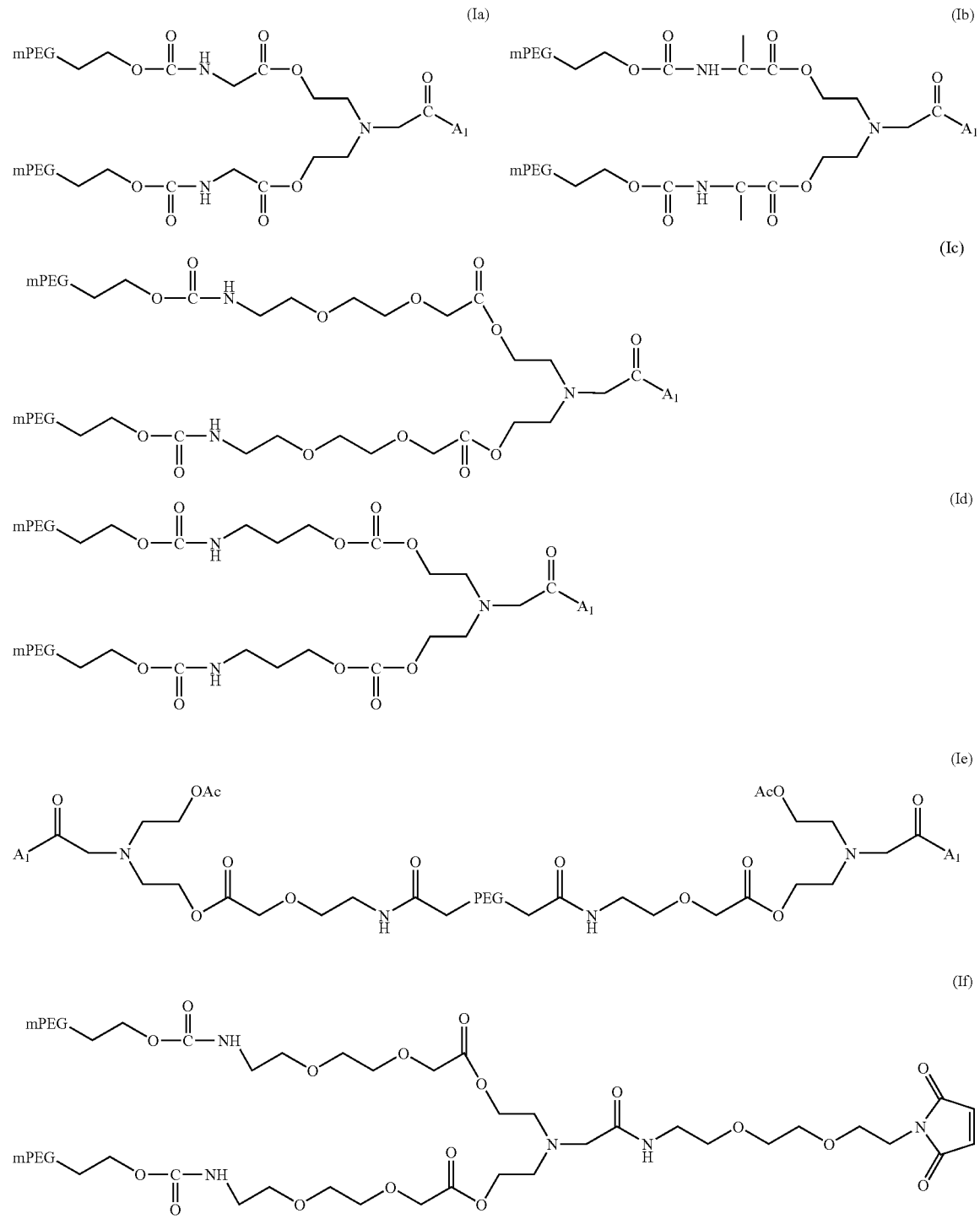

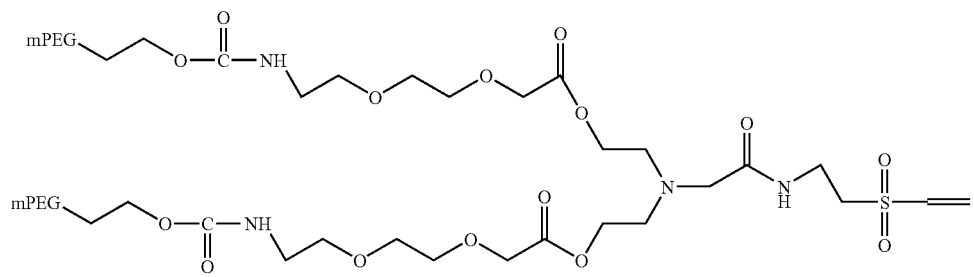
(Ig)
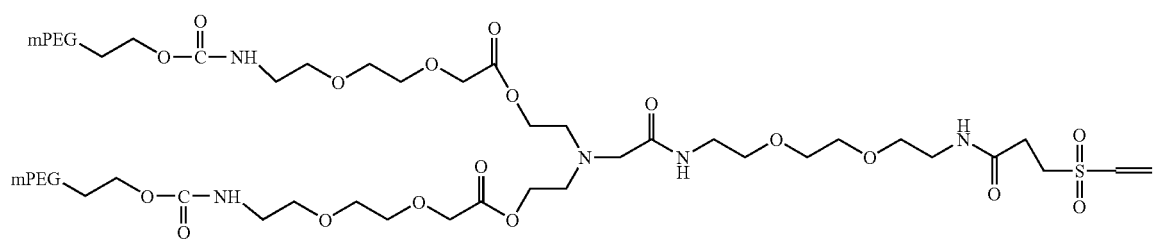
(Ih)
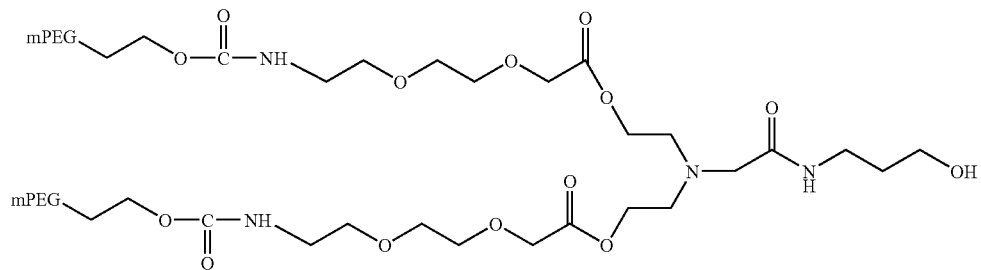
(Ii)
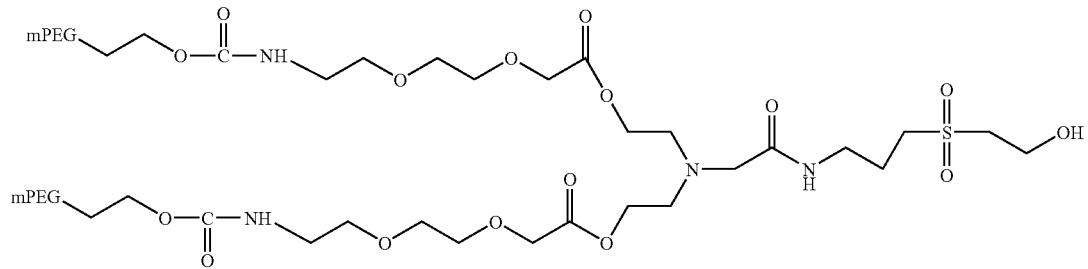
(Ij)
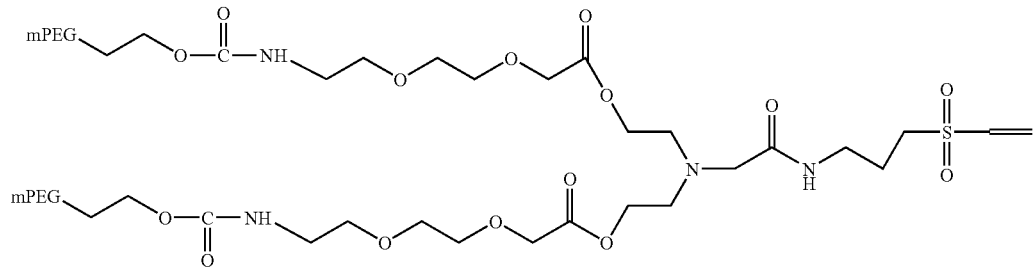
(Ik)

where $A_1$ is a leaving group such as

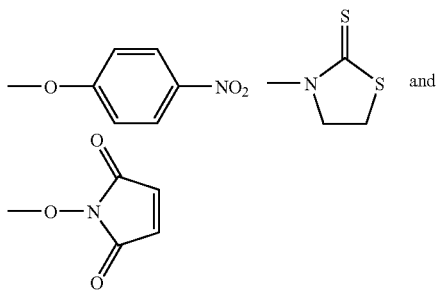

or other leaving groups such as those described above in section E 1. Reaction of the bicine-activated polymers with a suitable target results in the transformation of the activated polymer into conjugates, transforming $A_1$ into $A_2$, were $A_2$ is a residue of a biologically active moiety, spacer, etc.

G. Multiple Polymer Loading

In a still further aspect of the invention there are provided bicine-based multiple branched polymer compounds. In particular, the base bicine derivative is further modified to include one or more terminal branching groups. Preferably, the terminal branching groups are of the formula:

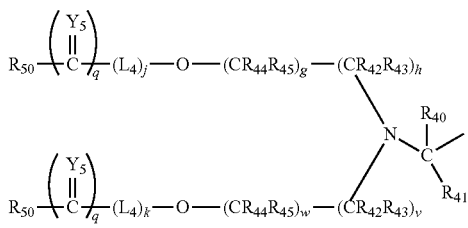

wherein:

$Y_5$ is O, S or $NR_{46}$;

$L_4$ is a bifunctional linker selected from the same group as that which defines $L_1$;

$R_{40}$-$R_{46}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

j and k are each independently 0 or a positive integer;

q is 0 or 1;

g, h, v and w are independently selected positive integers;

$R_{50}$ is selected from the group consisting of substantially non-antigenic polymer residues, $C_{1-6}$ alkyls, $C_{1-6}$ aralkyls, and

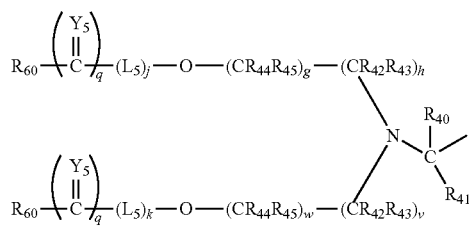

wherein:

$L_5$ is a bifunctional linker selected from the same group as that which defines $L_1$; and $R_{60}$ is selected from the group consisting of substantially non-antigenic polymer residues, $C_{1-6}$ alkyls and $C_{1-6}$ aralkyls.

The resulting branched bicine derivatives are of the formula structure:

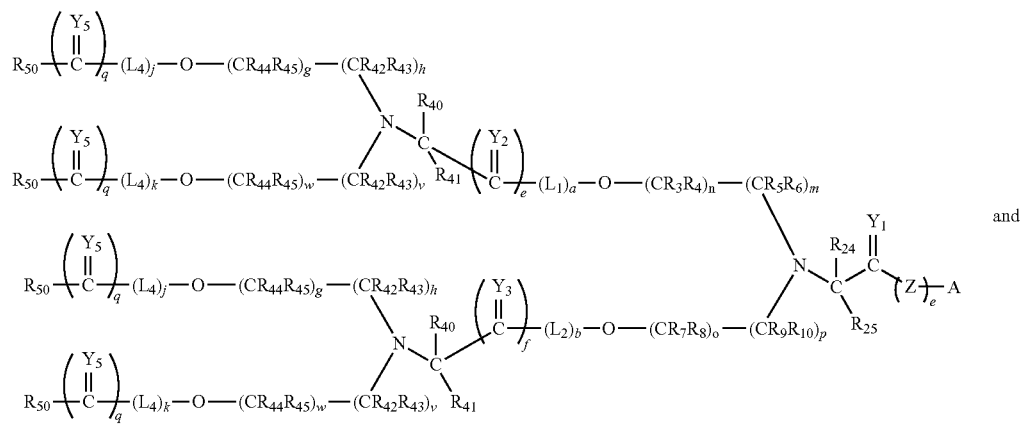

-continued

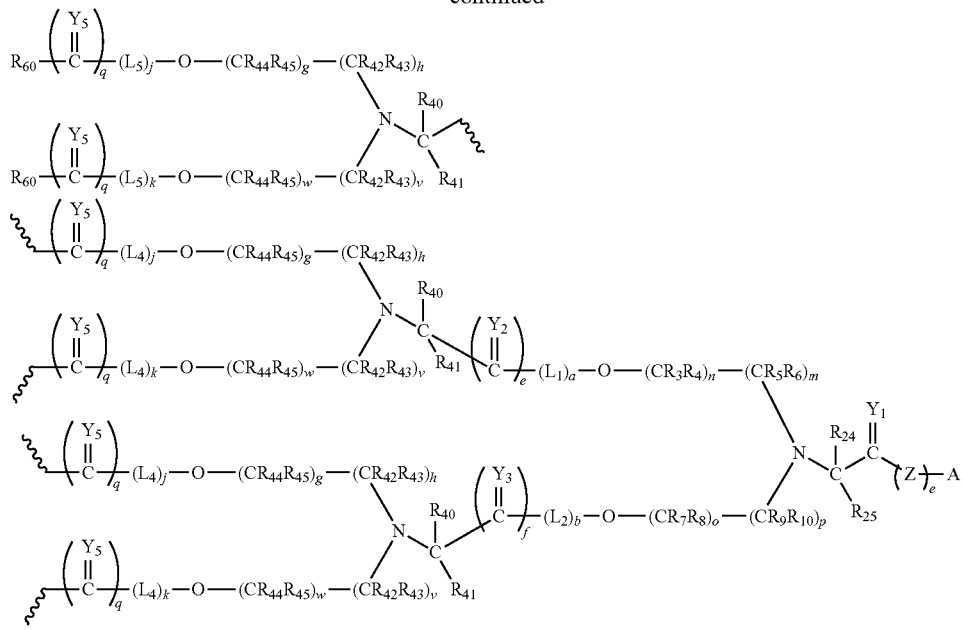

where all variables are as previously defined above.

As demonstrated below and in the examples, the bicine derivative intermediate containing the blocked primary amine is reacted with two equivalents of an activated bicine polymer to form a bicine polymer system containing up to four strands of polymer which are joined to a single point of attachment on the biologically active molecule, enzyme, target, etc. The process can be repeated to form the eight stranded derivative by reacting two equivalents of the four stranded polymer bicine derivative described above with one equivalent of the blocked primary amine bicine derivative.

H. Mixed Linker Systems

In another aspect of the invention there are provided bicine-based polymeric transport systems containing a second and different type of polymeric system attached to the biologically active moiety designated herein as A. The mixed linker or hybrid systems can be prepared by at least two methods. For example, the bicine-based system can be synthesized first as discussed above and then the bicine-attached biologically active moiety is PEGylated using any art-recognized activated polymer such as thiazolidinyl thione-, succinimidyl carbonate- or maleimide-activated PEG. Alternatively, the biologically active material can be PEGylated first and then reacted with the activated bicine based system described above. It will be understood that the mixed linker or hybrid systems will be better suited for proteins, enzymes and the like where multiple amino groups (e.g. E amino groups of lysines or N-terminal groups) cysteine or thio groups are available for attachment of the various polymer linkers. For purposes of the present invention, "activated polymers" will be understood to include polymers containing one or more terminal groups which are capable of reacting with one or more of amino groups, histidine nitrogens, carboxyl groups, sulfhydryl groups, etc. found on enzymes, proteins, etc., as well as such groups found on synthetically prepared organic compounds. It will further be appreciated that the activating groups can also be used to form the activated-bicine systems described above.

The activating terminal group is therefore any group which facilitates conjugation of the polymers with the biologically active material, i.e. protein, enzyme, etc. either before of after the double prodrug transport system of the present invention has been synthesized. See, for example, U.S. Pat. No. 4,179, 337 and commonly-assigned U.S. Pat. No. 6,113,906, the disclosure of each of which is hereby incorporated by reference.

I. In Vivo Diagnostics

A further aspect of the invention provides the conjugates of the invention optionally prepared with a diagnostic tag linked to the transport enhancer described above, wherein the tag is selected for diagnostic or imaging purposes. Thus, a suitable tag is prepared by linking any suitable moiety, e.g., an amino acid residue, to any art-standard emitting isotope, radio-opaque label, magnetic resonance label, or other non-radioactive isotopic labels suitable for magnetic resonance imaging, fluorescence-type labels, labels exhibiting visible colors and/or capable of fluorescing under ultraviolet, infrared or electrochemical stimulation, to allow for imaging tumor tissue during surgical procedures, and so forth. Optionally, the diagnostic tag is incorporated into and/or linked to a conjugated therapeutic moiety, allowing for monitoring of the distribution of a therapeutic biologically active material within an animal or human patient.

In a still further aspect of the invention, the inventive tagged conjugates are readily prepared, by art-known methods, with any suitable label, including, e.g., radioisotope labels. Simply by way of example, these include $^{131}$Iodine, $^{125}$Iodine, $^{99m}$Technetium and/or $^{111}$Indium to produce radio-immunoscintigraphic agents for selective uptake into tumor cells, in vivo. For instance, there are a number of art-known methods of linking peptide to Tc-99m, including, simply by way of example, those shown by U.S. Pat. Nos. 5,328,679; 5,888,474; 5,997,844; and 5,997,845, incorporated by reference herein.

Broadly, for anatomical localization of tumor tissue in a patient, the conjugate tag is administered to a patient or animal suspected of having a tumor. After sufficient time to allow the labeled immunoglobulin to localize at the tumor site(s), the signal generated by the label is detected, for instance, visually, by X-ray radiography, computerized transaxial tomography, MRI, by instrumental detection of a luminescent tag, by a photo scanning device such as a gamma camera, or any other method or instrument appropriate for the nature of the selected tag.

The detected signal is then converted to an image or anatomical and/or physiological determination of the tumor site. The image makes it possible to locate the tumor in vivo and to devise an appropriate therapeutic strategy. In those embodiments where the tagged moiety is itself a therapeutic agents, the detected signal provides evidence of anatomical localization during treatment, providing a baseline for follow-up diagnostic and therapeutic interventions.

J. Methods of Treatment

Another aspect of the present invention provides methods of treatment for various medical conditions in mammals. The methods include administering to the mammal in need of such treatment, an effective amount of a prodrug, such as a doxorubicin-bicine linked-PEG conjugate, which has been prepared as described herein. The compositions are useful for, among other things, treating neoplastic disease, reducing tumor burden, preventing metastasis of neoplasms and preventing recurrences of tumor/neoplastic growths in mammals.

The amount of the prodrug administered will depend upon the parent molecule, e.g. peptide, polypeptide, protein, enzyme, etc. included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. Those skilled in the art will determine the optimal dosing of the prodrug selected based on clinical experience and the treatment indication. Actual dosages will be apparent to the artisan without undue experimentation.

The compositions of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to mammals in need thereof.

EXAMPLES

The following examples serve to provide further appreciation of the invention but are not meant in any way to restrict the effective scope of the invention. The underlined and bold-faced numbers recited in the Examples correspond to those shown in FIGS. 1 to 17.

General Procedures. All reactions were run under an atmosphere of dry nitrogen or argon. Commercial reagents were used without further purification. All PEG compounds were dried under vacuum or by azeotropic distillation from toluene prior to use. NMR spectra were obtained using a Varian Mercury®300 NMR spectrometer and deuterated chloroform as the solvent unless otherwise specified. Chemical shifts ($\delta$) are reported in parts per million (ppm) downfield from tetramethylsilane (TMS).

HPLC Method. The reaction mixtures and the purity of intermediates and final products were monitored by a Beckman Coulter System Gold® HPLC instrument employing a ZOBAX® 300 SB C-8 reversed phase column (150×4.6 mm) or a Phenomenex Jupiter® 300A C18 reversed phase column (150×4.6 mm) with a multiwavelength UV detector, using a gradient of 30-90% of acetonitrile in 0.5% trifluoroacetic acid (TFA) at a flow rate of 1 mL/min.

Example 1

Synthesis of Compound (3)

A solution of 1 (24.0 g, 0.228 mol) and 2 (12.0 g, 0.061 mol) in anhydrous methylene chloride (DCM, 400 mL) was stirred at room temperature for 18 hrs. The reaction mixture was washed with water (4×150 mL), and the organic layer dried over anhydrous sodium sulfate, followed by filtration and removal of the solvent in vacuo to yield 3 (6.1 g, 0.0279 mol, 46%). $^{13}$C NMR (67.8 MHz, CDCl$_3$) $\delta$ 172.1, 81.4, 59.5, 57.0, 56.3, 27.8.

Example 2

Synthesis of Compound (4)

A solution of compound 3 (0.50 g, 2.28 mmol), N-trityl glycine (4.26 g, 13.4 mmol), 4,4'-dimethylaminopyridine (DMAP, 2.18 g, 17.8 mmol), and scandium triflate (0.65 g, 1.32 mmol) in anhydrous DCM (25 mL) was cooled to −8° C. in an ice-salt bath for 30 min. 1-(3-dimethylaminopropyl)-3-ethylcarbodiimide hydrochloride (EDC, 3.0 g, 15.6 mmol) was added and the reaction mixture stirred at −8° C. for 30 min and then at room temperature for 12 hrs. The reaction mixture was filtered and the filtrate washed with 0.1 N HCl (3×20 mL), distilled water (20 mL), dried (MgSO$_4$), and the solvent evaporated in vacuo. The product was further purified by silica gel column chromatography to give 4 (1.40 g, 1.71 mmol, 75%). $^{13}$C NMR (67.8 MHz, CDCl$_3$) $\delta$ 172.38, 170.67, 145.46, 128.71, 128.03, 126.61, 81.14, 70.67, 63.08, 56.18, 52.70, 45.79, 28.02.

Example 3

Synthesis of Compound (5)

Compound 4 (0.240 g, 0.292 mmol) was dissolved in 1% solution of trifluoroacetic acid (TFA) in DCM (10 mL) and stirred at room temperature for 30 min. The solvent was partially removed under reduced pressure and ethyl ether (50 mL) was added to precipitate the product. After decanting the ether, the residue was again dissolved in DCM and evaporated in vacuo to give 5 (0.148 g, 0.263 mmol, 90%). $^{13}$C NMR (67.8 MHz, CDCl$_3$/CD$_3$OD) $\delta$ 167.85, 166.81, 83.40, 61.81, 55.11, 52.78, 39.79, 27.47.

Example 4

Synthesis of Compound (6)

To a solution of monomethoxypoly(ethylene glycol) 4-nitrophenyl carbonate (mPEG-PNP, 12 kDa, 6.0 g, 0.49 mmol) and DMAP (0.12 g, 0.98 mmol) in anhydrous DCM (35 mL) was added dropwise of the solution of compound 5 (0.17 g, 0.30 mmol) in DCM/dimethylformamide (DMF) (32 mL/3 mL) over a time period of 30 min. The resulting mixture was stirred at room temperature for another 12 hrs. The solvent was partially removed under reduced pressure, followed by precipitation of the PEG derivative with ethyl ether. Filtration gave the crude PEG product which was crystallized from DCM/ethyl ether (24 mL/96 mL) and then from isopropanol (IPA, 120 mL) respectively to give 6 (5.6 g, 0.23 mmol, 76%). $^{13}$C NMR (67.8 MHz, CDCl$_3$) δ 170.16, 169.68, 156.10, 80.76, 63.11, 58.67, 58.52, 52.46, 42.23, 27.82.

Example 5

Synthesis of Compound (7)

PEG derivative 6 (5.6 g, 0.23 mmol) was dissolved in TFA/DCM (30 mL/60 mL) and stirred at room temperature for 12 hrs. The solvents were evaporated under reduced pressure. The residue was re-dissolved in 10 mL DCM and precipitated with ethyl ether, filtered and washed with several portions of ether to give 7 (5.1 g, 0.21 mmol, 91%). $^{13}$C NMR (67.8 MHz, CDCl$_3$) δ 171.25, 169.68, 156.21, 62.46, 58.66, 58.49, 52.82, 42.24.

Example 6

Synthesis of Compound (8)

A solution of 7 (5.1 g, 0.21 mmol), DMAP (0.076 g, 0.63 mmol), and 2-mecaptothiazoline (2-MT, 0.075 g, 0.63 mmol) in anhydrous DCM (70 mL) was cooled to 0° C. in an ice bath for 30 min, and EDC (0.12 g, 0.63 mmol) was added in one portion. The mixture was allowed to warm to room temperature slowly and stirred for 12 hrs. The solvent was partially removed under reduced pressure and the PEG linker precipitated with ethyl ether (200 mL). The crude product was obtained by filtration, and crystallized from DCM/ethyl ether (20 mL/80 mL) and then from isopropanol (IPA, 100 mL) respectively to give 8 (4.5 g, 0.18 mmol, 80%). $^{13}$C NMR (67.8 MHz, CDCl$_3$) δ 201.11, 172.70, 169.59, 156.03, 63.20, 58.44, 55.18, 52.37, 42.09, 28.53.

Example 7

Synthesis of Compound (9)

A solution of 8 (2.0 g, 0.082 mmol), doxorubicin hydrochloride (0.095 g, 0.16 mmol), and DMAP (0.040 g, 0.33 mmol) in anhydrous DMF/DCM (20 mL/20 mL) was stirred at room temperature for 12 hrs. The solvents were partially removed under reduced pressure and the final product was precipitated with ethyl ether (80 mL). The solid was filtered and recrystallized from DMF/methanol (35 mL/25 mL) to give 9 (1.75 g, 0.070 mmol, 86%). $^{13}$C NMR (67.8 MHz, CDCl$_3$) δ 212.93, 186.13, 169.95, 169.46, 160.68, 156.68, 155.95, 155.36, 135.73, 135.36, 133.80, 133.56, 119.78, 118.69, 111.46, 101.09, 75.63, 69.40-74.00 (PEG), 68.29, 65.53, 64.93, 63.16, 61.87, 60.25, 59.58, 57.35, 55.36, 45.46, 43.32, 36.51, 34.71, 30.74, 17.91.

Example 8

Synthesis of Compound (11)

A solution of compound 3 (0.60 g, 2.74 mmol), benzyloxycarbonyl alanine (3.61 g, 16.3 mmol), DMAP (2.64 g, 21.6 mmol), and scandium triflate (0.96 g, 1.95 mmol) in anhydrous DCM (72 mL) was cooled to −8° C. in an ice-salt bath for 30 min. Then 1,3-diisopropylcarbodiimde (DIPC, 2.42 g, 19.2 mmol) was added and the reaction mixture stirred at −8° C. for 30 min, and then at room temperature for 12 hrs. The reaction mixture was filtered, the filtrate washed with 0.1 N HCl (3×20 mL), distilled water (20 mL), dried (MgSO$_4$), and the solvent evaporated in vacuo. The product was further purified by silica gel column to give pure 11 (1.08 g, 1.71 mmol, 75%). $^{13}$C NMR (67.8 MHz, CDCl$_3$) δ 172.98, 170.64, 155.68, 136.25, 128.44, 128.04, 81.11, 66.62, 63.54, 56.06, 52.67, 49.43, 27.93, 18.19.

Example 9

Synthesis of Compound (12)

A suspension of 11 (0.60 g, 0.95 mmol) and palladium hydroxide/carbon (0.60 g) in ethanol (150 mL) was shaken at room temperature under 50 psi hydrogen pressure in a closed vessel for 24 hrs. The mixture was filtered and the solvent removed in vacuo to give 12 (0.29 g 0.81 mmol, 85%). $^{13}$C NMR (67.8 MHz, CDCl$_3$) δ 170.38, 81.70, 64.26, 56.43, 52.99, 49.40, 28.06, 15.92.

Example 10

Synthesis of Compound (13)

A solution of monomethoxypoly(ethylene glycol) succinimidyl carbonate (SC-mPEG, 12 kDa, 2.0 g, 0.164 mmol), compound 12 (0.030 g, 0.083 mmol) and DMAP (0.022 g, 0.183 mmol) in anhydrous chloroform (20 mL) was refluxed for 12 hrs. The solvent was partially removed under reduced pressure, followed by precipitation of the PEG derivative with ethyl ether. Filtration gave crude PEG product, which was crystallized from EPA (40 mL) to give 13 (1.5 g, 0.061 mmol, 74%). $^{13}$C NMR (67.8 MHz, CDCl$_3$) δ 172.46, 170.13, 155.22, 80.78, 63.28, 58.59, 55.82, 52.48, 49.16, 27.77, 18.03.

Example 11

Synthesis of Compound (14)

Compound 13 (1.5 g, 0.061 mmol) was dissolved in TFA/DCM (6.5 mL/13.5 mL) and stirred at room temperature for 24 hrs. The solvents were evaporated under reduced vacuum. The residue was dissolved in 5 mL DCM and precipitated by ethyl ether (80 mL), and filtered to give 14 (1.2 g, 0.049 mmol, 80%). $^{13}$C NMR (67.8 MHz, CDCl$_3$) δ 172.31, 168.23, 155.16, 63.18, 58.49, 55.82, 52.44, 49.15, 27.70, 17.92.

Example 12

Synthesis of Compound (15)

A solution of 14 (0.80 g, 0.033 mmol), DMAP (0.016 g, 0.13 mmol), and 2-MT (0.016 g, 0.13 mmol) in anhydrous DCM (10 mL) was cooled to 0° C. in an ice bath for 30 min, and EDC (0.025 g, 0.13 mmol) was then added. The mixture was allowed to warm to room temperature slowly and stirred for 12 hrs. The solvent was partially removed and the PEG linker was precipitated with ethyl ether (20 mL). The crude product was filtered, crystallized from DCM/ethyl ether (4 mL/16 mL) and finally recrystallized from EPA (20 mL) to give 15 (0.50 g, 0.020 mmol, 62%). The structure of the product is confirmed by NMR.

Example 13

Synthesis of Compound (16)

A solution of 15 (0.5 g, 0.020 mmol), daunorubicin hydrochloride (0.023 g, 0.041 mmol), and DMAP (0.005 g, 0.041 mmol) in anhydrous DMF/DCM (10 mL/10 mL) was stirred at room temperature for 12 hrs. The solvents were partially removed under reduced pressure and the final product was precipitated with ethyl ether (30 mL). The solid was filtered and crystallized from IPA (20 mL) to give 16 (0.4 g, 0.016 mmol, 80%). The structure of the product is confirmed by NMR.

Example 14

Synthesis of Compound (17)

A solution of di-tert-butylcarbonate (10.27 g, 47.2 mmol) in chloroform (40 mL) was added to a solution of 2-(2-aminoethoxy)-ethanol (5.0 g, 47.62 mmol) in chloroform (40 mL) and the mixture was stirred at room temperature for 1.5 hrs. The solution was washed with water (30 mL), the organic layer dried (MgSO$_4$), and concentrated in vacuo to give 2-(2-Boc-aminoethoxy)-ethanol (9.6 g, 99%). $^1$H NMR (300 MHz, CDCl$_3$) δ 5.43 (s, 1H), 3.43 (s, 1H), 3.56 (m, 4H), 3.73 (t, 2H, J=5.4 Hz), 3.32 (m, 2H), 1.45 (s, 9H); $^{13}$C NMR (67.8 MHz, CDCl$_3$) δ 156.06, 79.06, 77.18, 72.14, 70.08, 61.31, 40.21, 28.21.

To a solution of 2-(2-Boc-aminoethoxy)-ethanol (4.5 g, 24.39 mmol) in toluene (100 mL) was added 1.0 M potassium t-butoxide in t-butanol (36.6 □L, 36.6 mmol) between −10 to −20° C. for 1.5 hrs and followed by addition of ethyl bromoacetate (8.15 g, 48.78 mmol). The resulting mixture was stirred for 3 hrs at a temperature between −10 to −20° C., followed by the addition of 0.25 N HCl (50 mL). The organic layer was separated and dried over anhydrous MgSO$_4$. The solvent was removed and the residue purified using silica gel column chromatography (30 to 50% ethylacetate in hexane) to give [2-(2-Boc-aminoethoxy)-ethoxy]-acetic acid ethyl ester (4.0 g, 15.36 mmol, 63%). $^1$H NMR (300 MHz, CDCl$_3$) δ 5.20 (s, 1H), 4.22 (q, 2H, J=7.29 Hz), 4.14 (s, 2H), 3.66-3.75 (m, 4H), 3.55 (m, 2H), 3.31 (m, 2H), 1.44 (s, 9H), 1.29 (t, 3H, J=7.29 Hz); $^{13}$C NMR (67.8 MHz, CDCl$_3$ δ170.02, 155.72, 78.68, 70.52, 69.94, 68.29, 60.44, 40.04, 28.06, 13.85.

To a solution of NaOH (5.0 g, 0.125 mol) in H$_2$O (5 mL) was added ethanol (50 mL), and a solution of [2-(2-Boc-aminoethoxy)-ethoxy]-acetic acid ethyl ester (4.0 g, 15.36 mmol) in ethanol (40 mL) in an ice bath was then added drop-wise. The temperature was kept <20° C. during the addition. The mixture was stirred for 2 hrs, followed by acidification to pH 2.5 with 6N HCl. The mixture was filtered, the filter cake washed with ethanol, and the filtrate concentrated in vacuo. The residue was extracted with DCM/H$_2$O to give 17 (2.55 g, 11.52 mmol, 75%). $^1$H NMR (300 MHz, CDCl$_3$) δ 6.25 (br s, 1H), 5.31 (s, 1H), 5.20 & 3.31 (m, 2H), 4.20 (s, 2H), 3.66-3.75 (m, 4H), 3.55 (m, 2H), 1.45 (s, 9H); $^{13}$C NMR (67.8 MHz, CDCl$_3$) δ 173.38, 156.12, 80.05, 79.55, 70.77, 70.12, 68.20, 53.32, 40.15, 28.21.

Example 15

Synthesis of Compound (18)

A solution of 3 (0.10 g, 0.45 mmol), 17 (0.70 g, 2.66 mmol), DMAP (0.90 g, 7.38 mmol), and scandium triflate (0.022 g, 0.045 mmol) in anhydrous DCM (35 mL) was cooled to −8° C. in an ice-salt bath for 30 min, EDC (0.67 g, 3.49 mmol) was added and the reaction mixture was stirred at −8° C. for another 30 min and then at room temperature for 4.5 h. The reaction mixture washed with 0.1 N HCl (3×30 mL), 0.1 N NaHCO$_3$ (3×30 mL), distilled (30 mL) water, dried (Na$_2$SO$_4$), and the solvent evaporated to give compound 18 (0.33 g, 0.45 mmol, 100%). $^{13}$C NMR (67.8 MHz, CDCl$_3$) δ 170.28, 170.05, 155.73, 81.13, 78.99, 70.77, 70.18, 68.42, 62.96, 56.15, 52.87, 40.31, 28.37, 28.15.

Example 16

Synthesis of Compound (19)

Compound 18 (0.33 g, 0.45 mmol) was dissolved in 20% solution of TFA in DCM (10 mL) and stirred at room temperature for 15 min. The solvent was removed in vacuo, the residue dissolved in DCM, and then evaporated under reduced pressure several times to remove traces of TFA to give 19 (0.33 g, 0.45 mmol, 100%). $^{13}$C NMR (67.8 MHz, CDCl$_3$/CD$_3$OD) δ 170.08, 164.91, 84.56, 70.50, 69.60, 67.58, 66.33, 59.21, 52.99, 39.17, 27.42.

Example 17

Synthesis of Compound (20)

A solution of 12 kDa SC-mPEG (2.0 g, 0.164 mmol) in anhydrous DCM (10 mL) was added drop-wise over a time period of 1 hr a solution of compound 19 (0.15 g, 0.20 mmol) and DMAP (0.040 g, 0.327 mmol) in DCM (10 mL). The resulting mixture was stirred at room temperature for an additional 12 hrs, and the solvent partially removed under reduced pressure, followed by precipitation of PEG derivative with ethyl ether. Filtration gave crude PEG product which was then crystallized from IPA (40 mL) to give 20 (1.8 g, 0.073 mmol, 89%). $^{13}$C NMR (67.8 MHz, CDCl$_3$) δ 169.89, 169.65, 155.83, 63.42, 62.61, 58.53, 55.86, 52.55, 49.99, 27.84.

Example 18

Synthesis of Compound (21)

A solution of 20 (2.0 g, 0.081 mmol) in DCM/TFA (20 mL/10 mL) was stirred at room temperature for 8 hrs, followed by partial removal of the solvent under reduced pressure. The product was precipitated out with ethyl ether, collected by filtration, and washed with ethyl ether to yield 21 (1.8 g, 0.073 mmol, 90%). $^{13}$C NMR (67.8 MHz, CDCl$_3$) δ 40.32, 52.78, 55.28, 58.52, 62.29, 63.35, 66.58, 67.64, 68.02-71.41 (PEG), 155.82, 169.62.

Example 19

Synthesis of Compound (22)

A solution of 21 (1.8 g, 0.073 mmol), 2-MT (0.018 g, 0.147 mmol), and DMAP (0.054 g, 0.443 mmol) in anhydrous DCM (20 mL) was cooled to 0° C., followed by the addition of EDC (0.028 g, 0.147 mmol). This mixture was allowed to warm to room temperature and stirred for 12 hrs, followed by partial removal of the solvent by under reduced pressure. The product was precipitated with ethyl ether, collected by filtration, and crystallized from IPA (40 mL) to yield 22 (1.5 g, 0.061 mmol, 83%). $^{13}$C NMR (67.8 MHz, CDCl$_3$) δ 28.65, 40.34, 52.47, 53.63, 55.25, 58.50, 62.84, 63.37, 68.03, 69.06, 69.58-73.03 (PEG), 155.79, 169.60, 172.55 and 200.90 ppm.

Example 20

Synthesis of Compound (23)

To a solution of 22 (1.0 g, 0.041 mmol) and doxorubicin hydrochloride (0.047 g, 0.081 mmol) in a mixture of DCM/DMF (10 mL/10 mL) was added DMAP (0.020 g, 0.162 mmol). This mixture was stirred under nitrogen for 18 hrs, followed by partial removal of the solvent under reduced pressure. The PEG derivative was precipitated with ethyl ether, collected by filtration, and crystallized twice from DMF/IPA (4 mL/16 mL) to yield 23 (0.44 g, 0.018 mmol, 44%). $^{13}$C NMR (67.8 MHz, CDCl$_3$) δ 16.80, 29.77, 33.83, 35.59, 38.49, 40.66, 44.57, 54.20, 55.33, 56.53, 58.82, 63.71, 67.20, 67.34, 68.27, 69.40, 69.69-73.22 (PEG), 100.72, 111.34, 118.27, 119.56, 133.35, 133.49, 135.25, 135.48, 155.39, 155.93, 156.14, 160.75, 169.92, 170.14, 186.36, 186.73 and 213.35.

Example 21

Synthesis of Compound (24)

To a solution of tert-Butyl-N-(3-hydroxypropyl)-carbamate (3.00 g, 17.14 mmol) in anhydrous chloroform (60 mL) was added N,N'-disuccinimidyl carbonate (DSC, 5.48 g, 21.43 mmol) and anhydrous pyridine (1.73 mL, 21.43 mmol). The reaction mixture was stirred at room temperature for 12 hrs. The solution was filtered, washed with 0.5 M HCl solution (4×60 mL), dried (MgSO$_4$), filtered, and the solvent removed in vacuo to yield 24 (4.88 g, 15.43 mmol, 90%). $^{13}$C NMR (67.8 MHz, CDCl$_3$) δ 25.37, 28.27, 28.80, 36.71, 68.89, 79.29, 151.48, 155.85, 168.69.

Example 22

Synthesis of Compound (25)

A solution of 3 (0.30 g, 1.37 mmol), 24 (1.30 g, 4.11 mmol), and scandium triflate (0.067 g, 0.137 mmol) in anhydrous DCM (45 mL) was cooled to 0° C. in an ice bath for 30 min. DMAP (0.52 g, 4.26 mmol) was then added and the reaction mixture was allowed to warm to room temperature and stirred for 12 hrs. The reaction mixture was washed with 0.1 N HCl (3×30 mL), 0.1 N NaHCO$_3$ (3×30 mL), dried (Na$_2$SO$_4$), and the solvent evaporated, and the residue purified by column chromatography on silica gel to give 25 (0.275 g, 0.44 mmol, 32%). $^{13}$C NMR (67.8 MHz, CDCl$_3$) δ 170.41, 155.77, 155.05, 81.13, 79.14, 66.18, 65.40, 56.24, 53.00, 37.14, 29.14, 28.40, 28.18.

Example 23

Synthesis of Compound (26)

Compound 25 (0.388 g, 0.624 mmol) was dissolved in 20% solution of TFA in DCM (15 mL) and stirred at room temperature for 15 min. The solvent was removed by rotary evaporation and the residue was dissolved in chloroform and then evaporated under vacuum several times to give 26 (0.388 g, 0.624 mmol, 100%). $^{13}$C NMR (67.8 MHz, CDCl$_3$/CD$_3$OD) δ 164.93, 153.73, 84.39, 65.02, 62.26, 53.72, 53.20, 36.46, 27.31, 26.02.

Example 24

Synthesis of Compound (27)

A solution of m12 kDa PEG-PNP (10.0 g, 0.822 mmol) in anhydrous DCM/DMF (24 mL/16 mL) was added drop-wise of the portion (11 mL) of the solution of compound 26 (0.400 g, 0.617 mmol) and DMAP (0.152 g, 0.1.24 mmol) in DCM (15 mL) over a time period of 1 hr. The resulting mixture was stirred at room temperature for another 3 hrs, then was added another 2 mL of the above solution of 26. The last 2 mL of the solution was added after another 3 hrs along with DMAP (0.076 g, 0.62 mmol), and the reaction mixture was stirred for a further 12 hrs. The solvent was partially removed by rotary evaporation, followed by precipitation of PEG derivative with ethyl ether. Filtration gave crude PEG product which was then crystallized from IPA (200 mL) to give 27 (9.6 g, 0.789 mmol, 96%). $^{13}$C NMR (67.8 MHz, CDCl$_3$) δ 170.00, 155.91, 154.62, 80.71, 65.80, 64.91, 63.43, 58.64, 55.83, 52.62, 37.15, 28.71, 27.87.

Example 25

Synthesis of Compound (28)

A solution of 27 (4.6 g, 0.188 mmol) in DCM/TFA (50 mL/25 mL) was stirred at room temperature for 12 hrs, followed by partial removal of the solvent by rotary evaporation. The product was precipitated with ethyl ether, collected by filtration, and washed with ethyl ether to yield 28 (4.0 g, 0.163 mmol, 87%). $^{13}$C NMR (67.8 MHz, CDCl$_3$) δ 171.47, 156.00, 154.51, 65.51, 64.96, 63.48, 58.61, 55.27, 52.82, 37.14, 28.66.

Example 26

Synthesis of Compound (29)

A solution of 28 (4.0 g, 0.163 mmol), 2-MT (0.058 g, 0.491 mmol), and DMAP (0.080 g, 0.654 mmol) in anhydrous DCM (60 mL) was cooled to 0° C., followed by the addition of EDC (0.094 g, 0.491 mmol). This mixture was allowed to warm to room temperature and stirred for 12 hrs, followed by partial removal of the solvent in vacuo. The product was precipitated with ethyl ether, collected by filtration, and crystallized from IPA (80 mL) to yield 29 (3.6 g, 0.147 mmol, 90%). $^{13}$C NMR (67.8 MHz, CDCl$_3$) δ 200.97, 172.86, 155.97, 154.66, 66.07, 65.00, 63.54, 60.39, 58.73, 55.39, 52.67, 37.22, 28.78.

Example 27

Synthesis of Compound (30)

To a solution of 29 (2.0 g, 0.082 mmol) and doxorubicin hydrochloride (0.094 g, 0.163 mmol) in DMF (20 mL) was added DMAP (0.040 g, 0.326 mmol). This mixture was stirred under nitrogen at room temperature for 12 hrs. The PEG derivative was precipitated out with ethyl ether, filtered, recrystallized twice from DMF/IPA (8 mL/32 mL) to yield 30 (1.50 g, 0.0615 mmol, 75%). $^{13}$C NMR (67.8 MHz, CDCl$_3$) δ

213.24, 186.61, 186.17, 169.25, 160.57, 156.11, 155.82, 155.24, 154.57, 135.42, 135.03, 133.29, 120.37, 119.39, 118.15, 111.10, 110.90, 100.63, 73.50-69.20 (PEG), 68.53, 67.12, 65.32, 65.17, 64.98, 63.57, 58.70, 56.41, 53.66, 44.70, 37.16, 35.43, 33.59, 28.75, 26.73, 16.71.

Example 28

Synthesis of Compound (32)

A solution of 3 (0.30 g, 1.37 mmol), 31 (1.75 g, 4.11 mmol), and scandium triflate (0.067 g, 0.137 mmol) in anhydrous DCM (45 mL) is cooled to 0° C. in an ice bath for 30 min. DMAP (0.52 g, 4.26 mmol) is then added and the reaction mixture is allowed to warm to room temperature and stirred for 12 hrs. The reaction mixture is washed with 0.1 N HCl (3×30 mL), 0.1 N NaHCO$_3$ (3×30 mL), dried (Na$_2$SO$_4$), and the solvent evaporated, and the residue purified by column chromatography on silica gel to give 32. The structure of 32 is confirmed by NMR.

Example 29

Synthesis of Compound (33)

A solution of 32 (0.30 g, 0.36 mmol), and piperidine (0.062 g, 0.72 mmol) in anhydrous DCM (25 mL) is stirred at room temperature for 2 hrs. The solvent is evaporated under reduced pressure and the residue purified by column chromatography on silica gel to give 33. The structure of 33 is confirmed by NMR.

Example 30

Synthesis of Compound (34)

A solution of 3 (1.00 g, 4.57 mmol) and acetic anhydride (0.466 g, 4.57 mmol), and in anhydrous DCM (45 mL) is cooled to 0° C. in an ice bath for 15 min and the reaction mixture is allowed to warm to room temperature and stirred for 2 hrs. The reaction mixture is washed with 0.1 N NaHCO$_3$ (3×30 mL), dried (Na$_2$SO$_4$), and the solvent evaporated, and the residue purified by column chromatography on silica gel to give 34. The structure of 34 is confirmed by NMR.

Example 31

Synthesis of Compound (35)

A solution of 34 (1.04 g, 4.00 mmol), 17 (2.83 g, 12.00 mmol), and scandium triflate (1.77 g, 3.60 mmol) in anhydrous DCM (70 mL) is cooled to 0° C. in an ice bath for 30 min. DMAP (1.46 g, 12.00 mmol) is then added and the reaction mixture is allowed to warm to room temperature and stirred for 12 hrs. The reaction mixture is washed with 0.1 N HCl (3×30 mL), 0.1 N NaHCO$_3$ (3×30 mL), dried (Na$_2$SO$_4$), and the solvent evaporated, and the residue purified by column chromatography on silica gel to give 35. The structure of 35 is confirmed by NMR.

Example 32

Synthesis of Compound (36)

Compound 35 (1.52 g, 3.00 mmol) is dissolved in 20% solution of TFA in DCM (45 mL) and stirred at room temperature for 15 min. The solvent is removed under reduced pressure and the residue is dissolved in chloroform and then evaporated in vacuo several times to remove the TFA to give 36. The structure of 36 is confirmed by NMR.

Example 33

Synthesis of Compound (37)

A solution of 40 kDa PEG di-acid (20.0 g, 0.500 mmol), 36 (1.01 g, 2.00 mmol), and DMAP (0.976 g, 8.00 mmol) in anhydrous DCM (400 mL) is added EDC (0.769 g, 4.00 mmol) and the reaction mixture stirred at room temperature for 12 hrs. The solvent is removed under reduced pressure, the residue crystallized from IPA (400 mL) to give 37. The structure of 37 is confirmed by NMR.

Example 34

Synthesis of Compound (38)

Compound 38 is made under the same conditions of 28. The structure of 38 is confirmed by NMR.

Example 35

Synthesis of Compound (39)

Compound 39 is made under the same conditions of 29. The structure of 39 is confirmed by NMR.

Example 36

Synthesis of Compound (40)

Compound 40 is made under the same conditions of 30. The structure of 40 is confirmed by NMR.

Example 37

Synthesis of Compound (42)

A solution of maleic anhydride (0.196 g, 2.00 mmol), DMAP (0.244 g, 2.00 mmol), and 41 (0.496 g, 2.00 mmol) in DCM (40 mL) is stirred at room temperature for 2 hrs. The solvent is removed under reduced pressure to give 42. The structure of 42 is confirmed by NMR.

Example 38

Synthesis of Compound (43)

A solution of 42 (0.496 g, 2.00 mmol) and sodium acetate (0.82 g, 10.0 mmol) in acetonitrile (40 mL) is refluxed for 45 min. The solvent is removed under reduced pressure to give 43. The structure of 43 is confirmed by NMR.

Example 39

Synthesis of Compound (44)

Compound 43 (0.496 g, 2.00 mmol) is dissolved in 20% solution of TFA in DCM (45 mL) and stirred at room temperature for 15 min. The solvent is removed in vacuo and the residue is dissolved in chloroform and then evaporated under reduced pressure several times to remove the TFA to give 44. The structure of 44 is confirmed by NMR.

Example 40

Synthesis of Compound (45)

To a solution of 22 (6.10 g, 0.25 mmol) and 44 (0.328 g, 1.00 mmol) in DCM (120 mL) is added DMAP (0.122 g, 1.00 mmol). This mixture is stirred under nitrogen at room temperature for 12 hrs. The PEG derivative is precipitated out with ethyl ether, filtered, crystallized from IPA (120 mL) to yield 45. The structure of 45 is confirmed by NMR.

Example 41

Synthesis of Compound (47)

To a solution of 22 (6.10 g, 0.25 mmol) and 46 (0.121 g, 1.00 mmol) in DCM (120 mL) is added DMAP (0.122 g, 1.00 mmol). This mixture is stirred under nitrogen at room temperature for 12 hrs. The PEG derivative is precipitated out with ethyl ether, filtered, crystallized from IPA (120 mL) to yield 47. The structure of 47 is confirmed by NMR.

Example 42

Synthesis of Compound (49)

To a solution of 22 (6.10 g, 0.25 mmol) and 48 (0.536 g, 1.00 mmol) in DCM (120 mL) is added DMAP (0.122 g, 1.00 mmol). This mixture is stirred under nitrogen at room temperature for 12 hrs. The PEG derivative is precipitated out with ethyl ether, filtered, crystallized from IPA (120 mL) to yield 49. The structure of 49 is confirmed by NMR.

Example 43

Synthesis of Compound (52)

To a solution of 8 (6.10 g, 0.25 mmol) and 5 (0.0701 g, 0.125 mmol) in DCM (120 mL) is added DMAP (0.122 g, 1.00 mmol). This mixture is stirred under nitrogen at room temperature for 12 hrs. The PEG derivative is precipitated out with ethyl ether, filtered, crystallized from IPA (120 mL) to yield 50. The structure of 50 is confirmed by NMR. Compound 50 is treated with TFA under the same conditions of making compound 7 to give 51. The structure of 51 is confirmed by NMR. Compound 51 is then activated under the same conditions of making compound 8 to give 52. The structure of 52 is confirmed by NMR. 52 is reacted with Dox-HCl under the same conditions of making 9 to make 52a

Example 44

Synthesis of Compound (53)

Compound 53 is made under the same conditions as in Example 43 except compound 15 and 12 are used instead of compound 8 and 5 respectively. The structure of 53 is confirmed by NMR.

Example 45

Synthesis of Compound (54)

Compound 54 is made under the same conditions as in Example 43 except compound 22 and 19 are used instead of compound 8 and 5 respectively. The structure of 54 is confirmed by NMR.

Example 46

Synthesis of Compound (55)

Compound 55 is made under the same conditions as in Example 43 except compound 29 and 26 are used instead of compound 8 and 5 respectively. The structure of 55 is confirmed by NMR.

Example 47

Synthesis of Compound (56)

Compound 56 is made under the same conditions as in Example 43 except compound 52 is used instead of compound 8. The structure of 56 is confirmed by NMR.

Example 48

Synthesis of Compound (57)

Compound 57 is made under the same conditions as in Example 43 except compound 53 is converted into thiazolidine thione derivative and reacted with 12 instead of compound 8 and 5 respectively. The structure of 57 is confirmed by NMR.

Example 49

Synthesis of Compound (58)

Compound 58 is made under the same conditions as in Example 43 except compound 54 is converted into thiazolidine thione derivative and reacted with 19 are used instead of compound 8 and 5 respectively. The structure of 58 is confirmed by NMR.

Example 50

Synthesis of Compound (59)

Compound 59 is made under the same conditions as in Example 43 except compound 55 is converted into thiazolidine thione derivative and reacted with 26 are used instead of compound 8 and 5 respectively. The structure of 59 is confirmed by NMR.

Example 51

Synthesis of Bicin-Green Fluorescence Protein (GFP) Conjugates

Materials. Releasable PEG linker, compound 8, was used in the study. PBS (10 mM phosphate, pH 7.4, 138 mM NaCl, and 2.7 mM KCl) was purchased from Sigma Inc. (St. Louis, Mo.). Pre-cast 10% Tris-glycine SDS electrophoresis gel and the gel running buffer were obtained from Invitrogen (Carlsbad, Calif.). Rat plasma in EDTA was received on dry ice the same day when the animal was sacrificed.

Methods

I. Preparation and Purification of Green Fluorescence Protein. The GFP used in the experiments is an enhanced version, EGFP, with maximum excitation wavelength of 488 nm and maximum emission wavelength of 507-509 nm. The EGFP sequence (Santa Cruz Biotechnology, Inc., Santa Cruz, Calif.) was subcloned into pET22b vector containing a Histidine tag at the carboxyl terminal and was expressed in BL21 strain of E. coli (Novagen, Inc., Madison, Wis.) with IPTG induction. The soluble, cytosolic EGFP was purified to near homogeneity from bacterial supernatant using a Ni-column (Novagen, Inc., Madison, Wis.), followed by DEAE anion exchange chromatography (Pharmacia Biotech Products, Piscataway, N.J.). Fluorescence intensity was measured on the HITACHI F-2000 Fluorescence Spectrophotometer. A linear standard curve of the protein concentration (1-140 ng/ml in 15 mM Tris, pH 7.4 buffer) versus fluorescence intensity was used for protein concentration quantitation.

II. Conjugation of PEG to GFP and Purification of PEG-PEG Compounds. With fast stirring, compound 8 was added to GFP solution (2 mg/ml) in 0.05 M NaHCO$_3$, pH 8.1, at a molar ratio of 30:1 (8:GFP). The solution was stirred under N$_2$ at 25° C. in dark for 45 min. After 45 min, the pH of the solution was lowered by adding sodium phosphate buffer, pH 6.4, to a final concentration of 77 mM (final pH was 6.8). Free PEG was removed on Superdex 200 Hiload 16/60 column (Amersham Pharmacia Biotech, Piscataway, N.J.) using a Biocad Perfusion Chromatography Workstation. The elution buffer was comprised of 10 mM sodium phosphate and 140 mM NaCl at pH 6.8. The fractions that exhibited both absorbance at 280 nm and fluorescence were pooled and concentrated using ultrafree-15 centrifugal filter device with 30 k NMWL membrane (Millipore Corp., Bedford, Mass.). The yield of the purified conjugate was about 59%. The concentration of PEG-GFP was determined using BCA protein assay reagent (Pierce, Rockford, Ill.) and fluorescence intensity quantitation.

III. Pharmacokinetics of GFP and PEG-GFP Conjugates in Rats. Conscious rats were restrained and injected intravenously via the tail vein with either GFP or PEG-GFP at a dose of 5 mg/kg. Following compound administration, sampling of blood began as scheduled. Rats were lightly anesthetized with a 30% oxygen/70% carbon dioxide mixture and bled for 0.5 ml of whole blood via their retroorbital sinus. Whole blood was collected within an EDTA microtube and immediately processed for plasma. Plasma was snap frozen on dry ice and stored at −20° C. until further analysis.

IV Analysis of GFP and PEG-GFP Conjugate in Plasma and Release Process. The plasma samples were thawed from −20° C. to 4° C. A 10-ul aliquot of plasma containing GFP or PEG-GFP was diluted with 1 mL of 15 mM Tris at pH 7.4. After thoroughly mixing, the fluorescence intensity was measured using the HITACHI F-2000 Fluorescence Spectrophotometer. The autofluorescence generated from plasma alone was subtracted from all the samples, using 15 mM Tris buffer at pH 7.4 as a blank. For the release process, the plasma samples collected at different time points were thawed from −20° C. to 4° C., diluted with PBS, and analyzed on a Superdex 75 HR 10/30 column (Amersham Pharmacia Biotech, Piscataway, N.J.) using the Biocad Perfusion chromatogram. GFP has 21 free amines, 20 from lysine side chains and one from the N-terminus. All purified PEG-GFP conjugates had an apparent molecular weight of higher than 200,000 Da on 10% SDS electrophoresis gel when the reaction was carried out at a 30:1 molar ratio (PEG:GFP). The PEGylation number estimated on the gel was 10-14 PEG molecules per GFP.

Results

Pharmacokinetics and Pharmacokinetic Parameters of GFP and PEG-GFP Conjugates in Rats. The pharmacokinetic parameters, such as half-life ($t_{1/2}$), area under curve (AUC), clearance (CL), and mean residence time (MRT) of GFP and PEG-GFP conjugates were estimated using noncompartmental methods (Table 1). The data show that the half-life of GFP can increase to 156 fold and the clearance can decrease to 167 fold after it is PEGylated. A one-compartmental model was used to predict the curves of dose plasma concentration versus time course following a single intravenous dose administration. Results showed that the correlation between predicted and observed curves was above 93% for native GFP and 96% for the PEG-GFP. The pK data shows that the PEG-GFP conjugates using this bicine system, can release natural GFP over an extended time period.

TABLE 1

Pharmacokinetic Parameters of GFP and PEG-GFP in Rats

|  | $T_{1/2}$ (h) | AUC (hr · dose %) | CL (dose/AUC) | MRT (h) | Correlation (obs vs est) |
|---|---|---|---|---|---|
| GFP | 0.15 ± 0.013 | 0.15 ± 0.02 | 6.72 ± 0.81 | 0.22 ± 0.04 | 93% |
| PEG-GFP | 23.46 ± 2.61 | 23.77 ± 2.39 | 0.04 ± 0.00 | 33.85 ± 3.76 | 96% |

Table 2 below shows various prodrug release times corresponding to PEG bicine conjugates.

TABLE 2

Properties of BICIN-Doxorubicin (or Daunorubicin) conjugates

| | compound | | | |
|---|---|---|---|---|
| | 9 | 16 | 23 | 30 |
| mw | 24855 | 24894 | 25031 | 25072 |
| $t_{1/2}$ (h) in rat plasma | 10 | 15 | 5.5 | 12.5 |

We claim:

1. A compound comprising the formula:

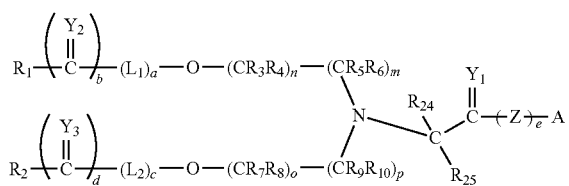

wherein:

R$_1$ and R$_2$ are independently selected from the group consisting of polyethylene glycol, C$_{1-6}$ alkyls, aralkyls, and terminal branching groups;

Y$_{1-3}$ are independently O, S or NR$_{11}$;

L$_1$ and L$_2$ are independently selected bifunctional linkers;

Z is selected from the group consisting of

wherein $L_3$ is a bifunctional linker and $Y_4$ is O, S or $NR_{11}$, hydrophobic moieties, bifunctional linking moieties and combinations thereof;

$R_3$-$R_{11}$, $R_{24}$ and $R_{25}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

A is an organic compound containing an amine;

a and c are each independently 0 or a positive integer;

b, d and e are independently 0 or 1; and m, n, o, and p are independently selected positive integers, provided that at least one of $R_1$ and $R_2$ is a polyethylene glycol and the weight average molecular weight thereof is about 40,000 Da.

2. The compound of claim 1, wherein A is selected from the group consisting of cardiovascular agents, anti-neoplastic agents, anti-infective agents, anti-fungal agents, anti-anxiety agents, gastrointestinal agents, central nervous system-activating agents, analgesic agents, fertility agents, contraceptive agents, anti-inflammatory agents, and steroidal agents.

3. The compound of claim 1, wherein $R_1$ is a polyethylene glycol; $R_2$ is $C_{1-6}$ alkyl; and both c and d are zero.

4. The compound of claim 1, wherein $R_3$-$R_{10}$, $R_{24}$ and $R_{25}$ are each hydrogen.

5. The compound of claim 1, wherein a, b, c, d, m, n, o and p are each 1 and e is 0 or 1.

6. The compound of claim 1, wherein $R_1$ comprises a polyalkylene oxide.

7. The compound of claim 1, wherein $R_2$ comprises a polyalkylene oxide.

8. The compound of claim 1, wherein $R_1$ comprises a polyethylene glycol.

9. The compound of claim 1, wherein $R_2$ comprises a polyethylene glycol.

10. The compound of claim 1, wherein $R_1$ or $R_2$ further include a capping group J, selected from the group consisting of OH, $NH_2$, SH, $CO_2H$, $C_{1-6}$ alkyl moieties,

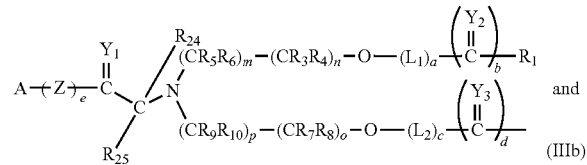

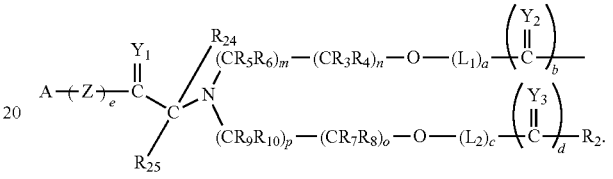

11. A compound of claim 10, selected from the group consisting of:

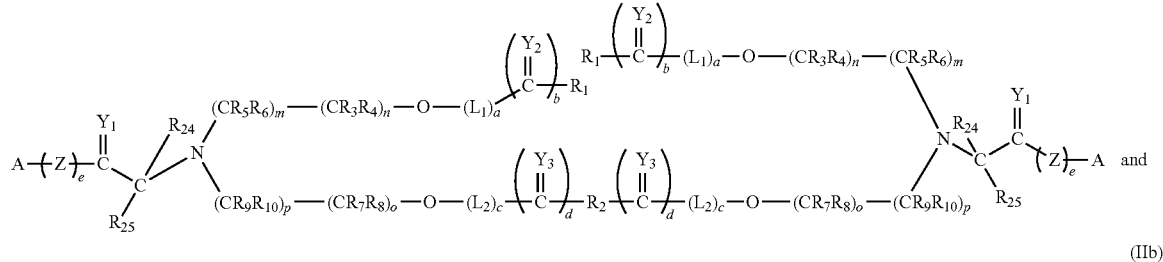

wherein $L_3$ is a bifunctional linker and $Y_4$ is O, S or $NR_{11}$.

12. The compound of claim 1, wherein $R_1$ is selected from the group consisting of:

J-O—$(CH_2CH_2O)_x$—,

J-O—$(CH_2CH_2O)_x$—$CH_2C(O)$—O—,

J-O—$(CH_2CH_2O)_x$—$CH_2CH_2NR_{12}$—,

J-O—$(CH_2CH_2O)_x$—$CH_2CH_2S$—,

—$OC(O)CH_2$—O—$(CH_2CH_2O)_x$—$CH_2C(O)$—O—,

—NR₁₂CH₂CH₂—O—(CH₂CH₂O)ₓ—CH₂CH₂NR₁₂— and

—SCH₂CH₂—O—(CH₂CH₂O)ₓ—CH₂CH₂S— wherein:

x is the degree of polymerization;

R₁₂ is selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; and J is a capping group.

13. The compound of claim 1, wherein R₁ and R₂ are individually selected from the group consisting of:

CH₃—O—(CH₂CH₂O)ₓ—,

CH₃—O—(CH₂CH₂O)ₓ—CH₂C(O)—O—,

CH₃—O—(CH₂CH₂O)ₓ—CH₂CH₂NH— and

CH₃—O—(CH₂CH₂O)ₓ—CH₂CH₂S— wherein x is the degree of polymerization.

14. The compound of claim 1, wherein R₂ is selected from the group consisting of:

J-O—(CH₂CH₂O)ₓ—,

J-O—(CH₂CH₂O)ₓ—CH₂C(O)—O—,

J-O—(CH₂CH₂O)ₓ—CH₂CH₂NR₁₃—,

J-O—(CH₂CH₂O)ₓ—CH₂CH₂S—,

—OC(O)CH₂—O—(CH₂CH₂O)ₓ—CH₂C(O)—O—,

—NR₁₃CH₂CH₂—O—(CH₂CH₂O)ₓ—CH₂CH₂NR₁₃— and

—SCH₂CH₂—O—(CH₂CH₂O)ₓ—CH₂CH₂S—, wherein:

x is the degree of polymerization;

R₁₃ is selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; and J is a capping group.

15. The compound of claim 1, wherein R₁ and R₂ each comprise a polymer residue of the formula —O—(CH₂CH₂O)ₓ and x is the degree of polymerization.

16. The compound of claim 15, wherein R₁ and R₂ each have a weight average molecular weight of from about 2,000 Da to about 25,000 Da.

17. The compound of claim 1, wherein L₁ is selected from the group consisting of:

—NH(CH₂CH₂O)₂CH₂C(O)—,

—NH(CH₂)₃OC(O)—,

—(CH₂)ᵥC(O)—,

—C(O)NH(CH₂)ᵥC(O)—,

—NH(CH₂)ᵥC(O)—,

—NR₁₉(CH₂)ₜ(CH₂CH₂O)_qNHC(O)—,

—(CH₂CH₂O)ₜNHC(O)—,

—O(CR₁₄R₁₅)ₜNHC(O)—,

—NR₁₉(CR₁₄R₁₅)_qC(O)NH(CR₁₆R₁₇)ₜC(O)—,

—O(CH₂)ₜOC(O)—,

—NR₁₉(CR₁₄R₁₅)ₜC(O)—,

—NR₁₉(CH₂CH₂O)ₜ—OC(O)—,

—O(CR₁₄R₁₅)ₜOC(O)—,

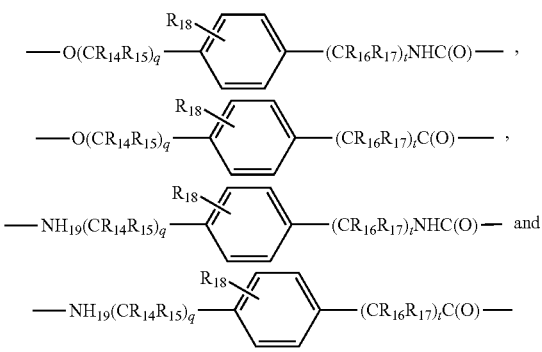

wherein $R_{14}$-$R_{17}$ and $R_{19}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

R₁₈ is selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, $NO_2$, haloalkyl and halogen; and t and q are individually selected positive integers.

18. The compound of claim 1, wherein L₂ is selected from the group consisting of:

—NH(CH₂CH₂O)₂CH₂C(O)—,

—NH(CH₂)₃OC(O)—,

—(CH₂)ᵥC(O)—,

—C(O)(CH₂)ᵥNHC(O)—,

—NH(CH₂)ᵥC(O)—,

—NR₂₅(CH₂)ᵥ(CH₂CH₂O)_wNHC(O)—,

—(CH₂CH₂O)ᵥNHC(O)—,

—O(CR₂₀R₂₁)ᵥNHC(O)—,

—NR₂₅(CR₂₀R₂₁)_w(O)CNH(CR₂₂R₂₃)ᵥC(O)—,

—O(CH₂)ᵥOC(O)—,

—NR₂₅(CR₂₀R₂₁)ᵥC(O)—,

—NR₂₅(CH₂CH₂O)ᵥ—OC(O)—,

—O(CR₂₀R₂₁)ᵥOC(O)—,

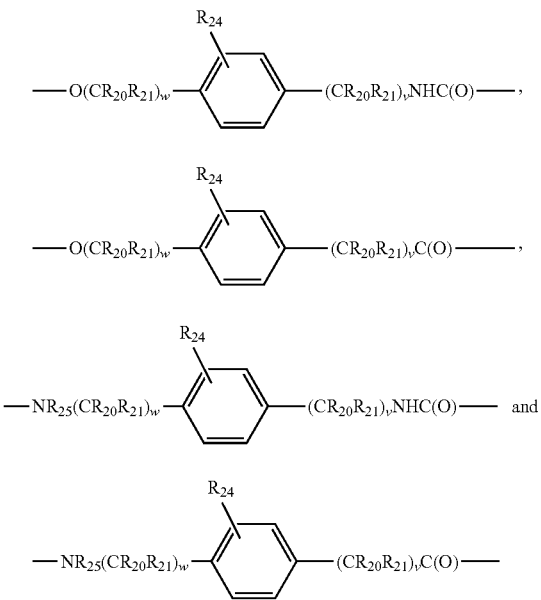

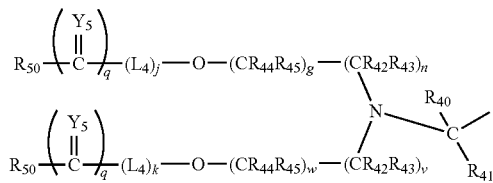

wherein
- $R_{20}$-$R_{23}$ and $R_{25}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
- $R_{24}$ is selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy, $NO_2$, haloalkyl and halogen; and
- v and w are individually selected positive integers.

19. The compound of claim 1, wherein said terminal branching group comprises the formula:

wherein:
- $Y_5$ is O, S or $NR_{46}$;
- $L_4$ is a bifunctional linker;
- $R_{40}$-$R_{46}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
- j and k are each independently 0 or a positive integer;
- q is 0 or 1;
- g, h, v and w are independently selected positive integers;
- $R_{50}$ is selected from the group consisting of substantially non-antigenic polymer residues, $C_{1-6}$ alkyls, $C_{1-6}$ aralkyls, and

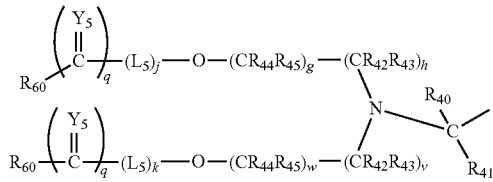

wherein:
- $L_5$ is a bifunctional linker; and
- $R_{60}$ is selected from the group consisting of substantially non-antigenic polymer residues, $C_{1-6}$ alkyls and $C_{1-6}$ aralkyls.

20. A compound of claim 19, comprising the structure:

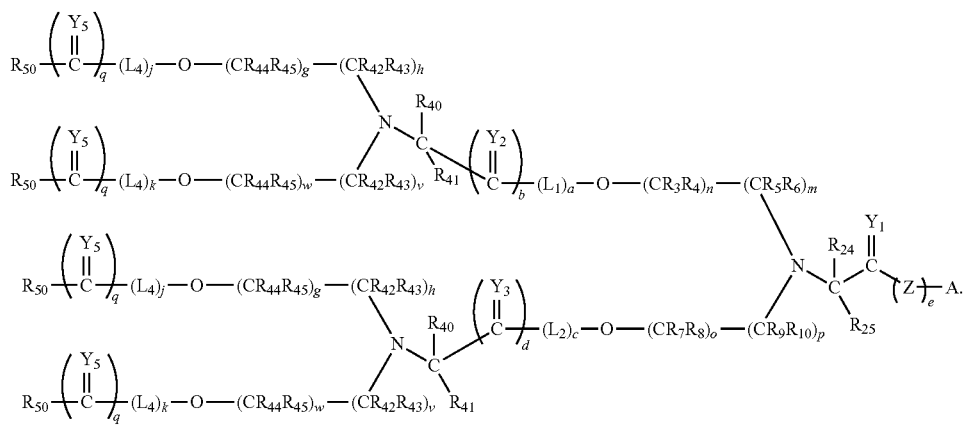

21. A compound of claim 19, comprising the structure:

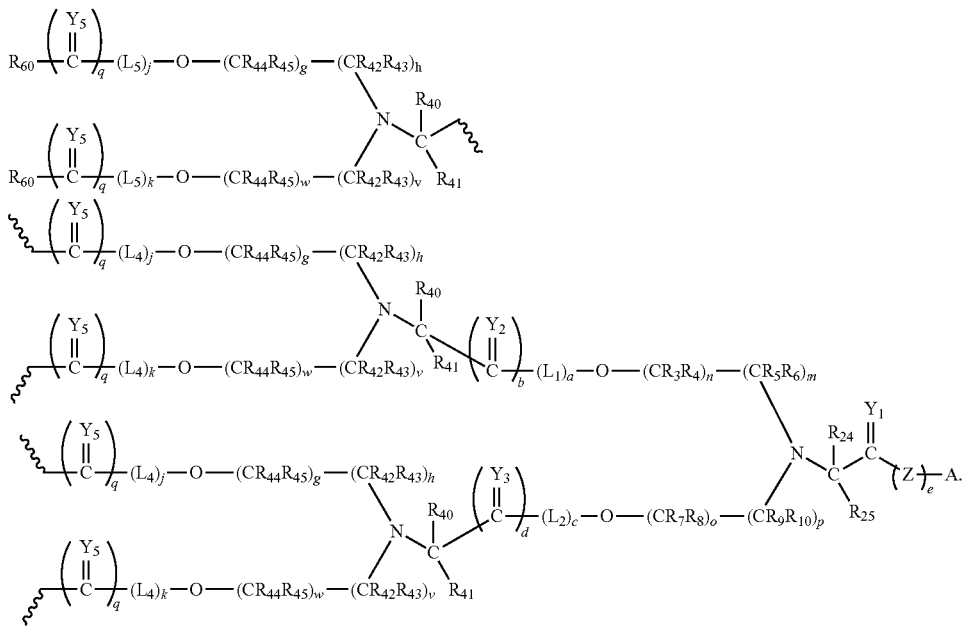

22. The compound of claim 1, wherein $R_3$-$R_{10}$, $R_{24}$ and $R_{25}$ are each hydrogen; $Y_1$ is oxygen; and $R_1$ is a polyethylene glycol.

23. The compound of claim 22, wherein a, b, c, d, m, n, o and p are each 1; and e is 0 or 1.

24. A method of treatment of a condition that is treatable by a moiety A of claim 2, comprising administering to a mammal in need thereof, an effective amount of a compound of claim 4, wherein $R_1$ is a polyethylene glycol.

25. A compound comprising the formula:

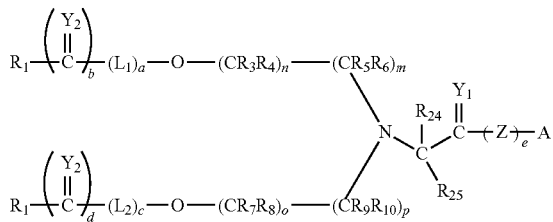

wherein:

$R_1$ and $R_2$ are independently selected from the group consisting of substantially non-antigenic polymer residues, $C_{1-6}$ alkyls, aralkyls, and terminal branching groups;

$Y_{1-3}$ are independently O, S or $NR_{11}$;

$L_1$ and $L_2$ are independently selected bifunctional linkers;

Z is selected from the group consisting of

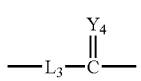

wherein $L_3$ is a bifunctional linker and $Y_4$ is O, S or $NR_{11}$, hydrophobic moieties, bifunctional linking moieties and combinations thereof;

$R_3$-$R_{11}$, $R_{24}$ and $R_{25}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

A is selected from the group consisting of proteins, and enzymes;

a and c are each independently 0 or a positive integer;

b, d and e are independently 0 or 1; and m, n, o, and p are independently selected positive integers, provided that at least one of $R_1$ and $R_2$ is a substantially non-antigenic polymer.

26. The compound of claim 25, wherein A is selected from the group consisting of cardiovascular agents, anti-neoplastic agents, anti-infective agents, anti-fungal agents, anti-anxiety agents, gastrointestinal agents, central nervous system-activating agents, analgesic agents, fertility agents, contraceptive agents and anti-inflammatory agents.

27. The compound of claim 25, wherein $R_3$-$R_{10}$, $R_{24}$ and $R_{25}$ are each hydrogen.

28. The compound of claim 25, wherein a, b, c, d, m, n, o and p are each 1 and e is 0 or 1.

29. The compound of claim 25, wherein $R_1$ comprises a polyalkylene oxide.

30. The compound of claim 25, wherein $R_2$ comprises a polyalkylene oxide.

31. The compound of claim 25, wherein $R_1$ comprises a polyethylene glycol.

32. The compound of claim 25, wherein $R_2$ comprises a polyethylene glycol.

33. The compound of claim 25, wherein $R_1$ or $R_2$ further include a capping group J, selected from the group consisting of OH, $NH_2$, SH, $CO_2H$, $C_{1-6}$ alkyl moieties,

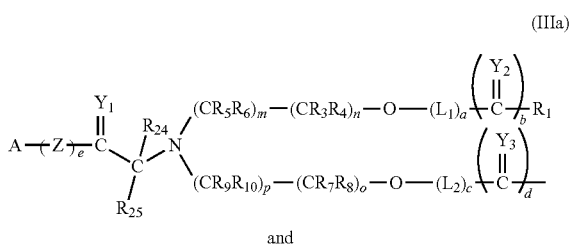

(IIIa)

and

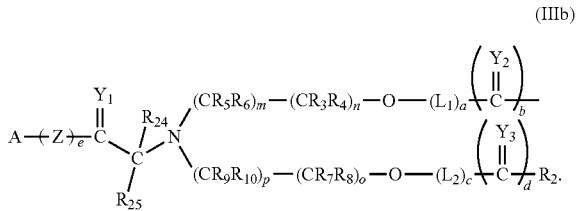

(IIIb)

34. A compound of claim 33, selected from the group consisting of:

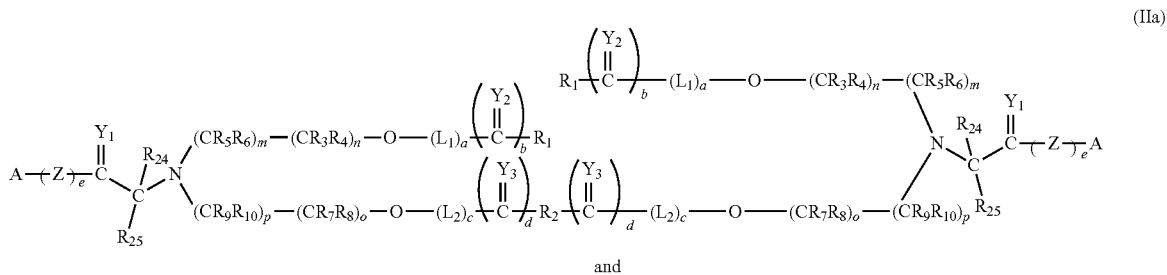

(IIa)

and

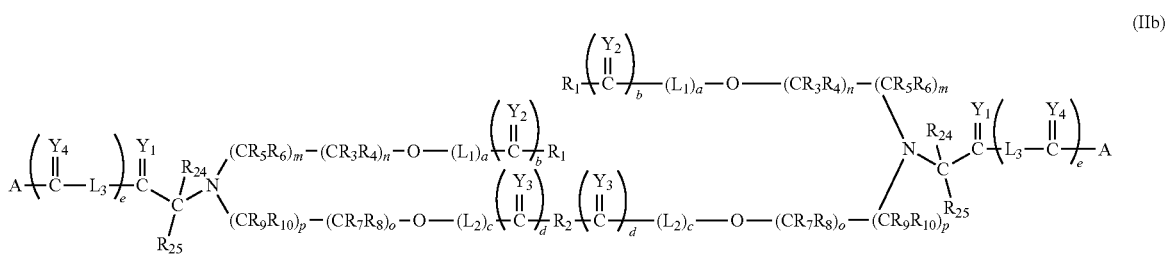

(IIb)

wherein $L_3$ is a bifunctional linker and $Y_4$ is O, S or $NR_{11}$.

35. The compound of claim 25, wherein $R_1$ is selected from the group consisting of:

J-O—$(CH_2CH_2O)_x$—,

J-O—$(CH_2CH_2O)_x$—$CH_2C(O)$—O—,

J-O—$(CH_2CH_2O)_x$—$CH_2CH_2NR_{12}$—,

J-O—$(CH_2CH_2O)_x$—$CH_2CH_2S$—,

—$OC(O)CH_2$—O—$(CH_2CH_2O)_x$—$CH_2C(O)$—O—,

—$NR_{12}CH_2CH_2$—O—$(CH_2CH_2O)_x$—$CH_2CH_2NR_{12}$— and

—$SCH_2CH_2$—O—$(CH_2CH_2O)_x$—$CH_2CH_2S$— wherein:

x is the degree of polymerization;

$R_{12}$ is selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; and J is a capping group.

36. The compound of claim 25, wherein $R_1$ and $R_2$ are individually selected from the group consisting of:

$CH_3$—O—$(CH_2CH_2O)_x$—, $CH_3$—O—$(CH_2CH_2O)_x$—$CH_2C(O)$—O—, $CH_3$—O—$(CH_2CH_2O)_x$—$CH_2CH_2NH$— and $CH_3$—O—$(CH_2CH_2O)_x$—$CH_2CH_2S$— wherein x is the degree of polymerization.

37. The compound of claim 35, wherein $R_2$ is selected from the group consisting of:

J-O—$(CH_2CH_2O)_x$—,

J-O—$(CH_2CH_2O)_x$—$CH_2C(O)$—O—,

J-O—$(CH_2CH_2O)_x$—$CH_2CH_2NR_{13}$—,

J-O—$(CH_2CH_2O)_x$—$CH_2CH_2S$—,

—$OC(O)CH_2$—O—$(CH_2CH_2O)_x$—$CH_2C(O)$—O—,

—$NR_{13}CH_2CH_2$—O—$(CH_2CH_2O)_x$—$CH_2CH_2NR_{13}$— and

—$SCH_2CH_2$—O—$(CH_2CH_2O)_x$—$CH_2CH_2S$—, wherein:

x is the degree of polymerization;

$R_{13}$ is selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; and J is a capping group.

38. The compound of claim 25, wherein $R_1$ and $R_2$ each comprise a polymer residue of the formula —O—$(CH_2CH_2O)_x$ and x is the degree of polymerization.

39. The compound of claim 30, wherein $R_1$ and $R_2$ each have a weight average molecular weight of from about 2,000 Da to about 25,000 Da.

40. The compound of claim 25, wherein $L_1$ is selected from the group consisting of:

—NH(CH$_2$CH$_2$O)$_2$CH$_2$C(O)—,

—NH(CH$_2$)$_3$OC(O)—,

—(CH$_2$)$_t$C(O)—,

—C(O)NH(CH$_2$)$_t$C(O)—,

—NH(CH$_2$)$_t$C(O)—,

—NR$_{19}$(CH$_2$)$_t$(CH$_2$CH$_2$O)$_q$NHC(O)—,

—(CH$_2$CH$_2$O)$_t$NHC(O)—,

—O(CR$_{14}$R$_{15}$)$_t$NHC(O)—,

—NR$_{19}$(CR$_{14}$R$_{15}$)$_q$C(O)NH(CR$_{16}$R$_{17}$)$_t$C(O)—,

—O(CH$_2$)$_t$OC(O)—,

—NR$_{19}$(CR$_{14}$R$_{15}$)$_t$C(O)—,

—NR$_{19}$(CH$_2$CH$_2$O)$_t$—OC(O)—,

—O(CR$_{14}$R$_{15}$)$_t$OC(O)—,

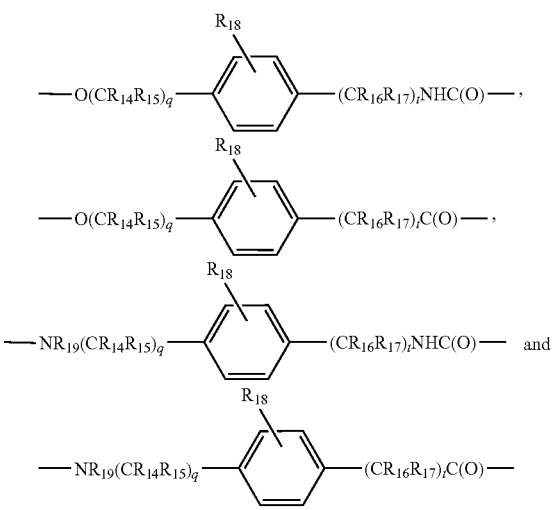

wherein $R_{14}$-$R_{17}$ and $R_{19}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$R_{18}$ is selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, NO$_2$, haloalkyl and halogen; and t and q are individually selected positive integers.

41. The compound of claim 25, wherein $L_2$ is selected from the group consisting of:

—NH(CH$_2$CH$_2$O)$_2$CH$_2$C(O)—,

—NH(CH$_2$)$_3$OC(O)—,

—(CH$_2$)$_v$C(O)—,

—C(O)(CH$_2$)$_v$NHC(O)—,

—NH(CH$_2$)$_v$C(O)—,

—NR$_{25}$(CH$_2$)$_v$(CH$_2$CH$_2$O)$_w$NHC(O)—,

—(CH$_2$CH$_2$O)$_v$NHC(O)—,

—O(CR$_{20}$R$_{21}$)$_v$NHC(O)—,

—NR$_{25}$(CR$_{20}$R$_{21}$)$_w$(O)CNH(CR$_{22}$R$_{23}$)$_v$C(O)—,

—O(CH$_2$)$_v$OC(O)—,

—NR$_{25}$(CR$_{20}$R$_{21}$)$_v$C(O)—,

—NR$_{25}$(CH$_2$CH$_2$O)$_v$—OC(O)—,

—O(CR$_{20}$R$_{21}$)$_v$OC(O)—,

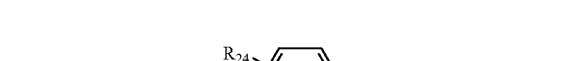

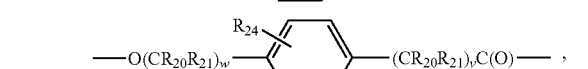

—NH$_{25}$(CR$_{20}$R$_{21}$)$_w$—⟨Ar(R$_{24}$)⟩—(CR$_{20}$R$_{21}$)$_v$C(O)— wherein $R_{20}$-$R_{23}$ and $R_{25}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$R_{24}$ is selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, $C_{1-6}$ heteroalkoxy, NO$_2$, haloalkyl and halogen; and v and w are individually selected positive integers.

42. The compound of claim 25, wherein said terminal branching group comprises the formula:

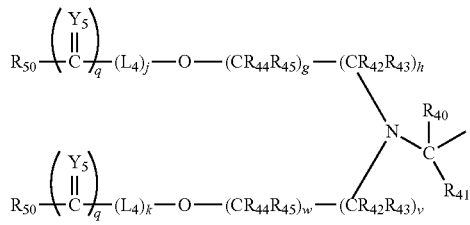

wherein:
$Y_5$ is O, S or $NR_{46}$;
$L_4$ is a bifunctional linker;
$R_{40}$-$R_{46}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
j and k are each independently 0 or a positive integer;
q is 0 or 1;
g, h, v and w are independently selected positive integers;
$R_{50}$ is selected from the group consisting of substantially non-antigenic polymer residues, $C_{1-6}$ alkyls, $C_{1-6}$ aralkyls, and

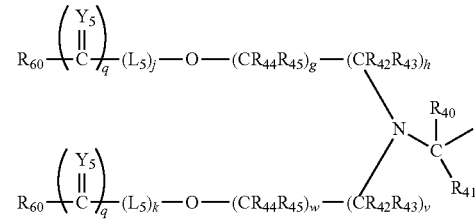

wherein:
$L_5$ is a bifunctional linker; and
$R_{60}$ is selected from the group consisting of substantially non-antigenic polymer residues, $C_{1-6}$ alkyls and $C_{1-6}$ aralkyls.

43. A compound of claim 42, comprising the structure:

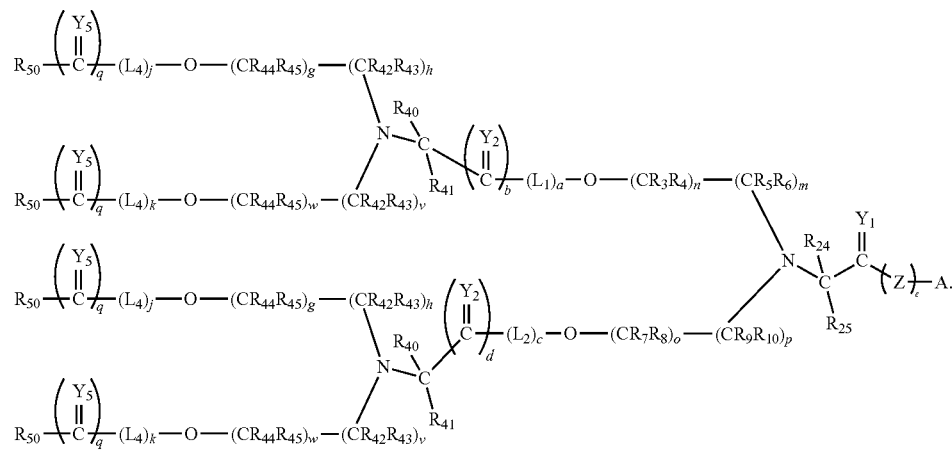

44. A compound of claim 42, comprising the structure:

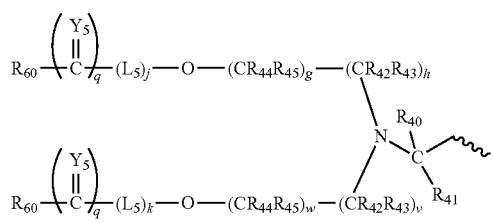

-continued
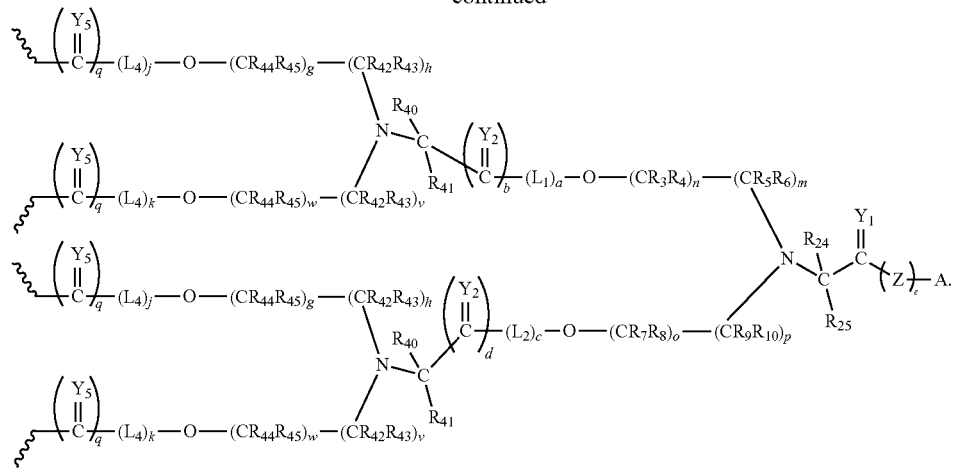
* * * * *